United States Patent
Matsuda et al.

(10) Patent No.: US 10,624,800 B2
(45) Date of Patent: Apr. 21, 2020

(54) FIXING MEMBER AND ABSORBENT ARTICLE

(71) Applicant: 3M INNOVATIVE PROPERTIES COMPANY, St. Paul, MN (US)

(72) Inventors: Yoshihisa Matsuda, Kanagawa (JP); Kristopher K. Biegler, Minneapolis, MN (US); Ryan M. Luepke, New Brighton, MN (US); Thomas J. Gilbert, St. Paul, MN (US); Hiroshi Sakurai, Kanagawa (JP)

(73) Assignee: 3M Innovative Properties Company, St. Paul, MN (US)

( * ) Notice: Subject to any disclaimer, the term of this patent is extended or adjusted under 35 U.S.C. 154(b) by 416 days.

(21) Appl. No.: 15/303,645

(22) PCT Filed: Apr. 10, 2015

(86) PCT No.: PCT/US2015/025260
§ 371 (c)(1),
(2) Date: Oct. 12, 2016

(87) PCT Pub. No.: WO2015/160642
PCT Pub. Date: Oct. 22, 2015

(65) Prior Publication Data
US 2017/0027776 A1 Feb. 2, 2017

(30) Foreign Application Priority Data
Apr. 14, 2014 (JP) .................................. 2014-082995

(51) Int. Cl.
*A61F 13/15* (2006.01)
*A61F 13/62* (2006.01)
(Continued)

(52) U.S. Cl.
CPC ...... *A61F 13/622* (2013.01); *A61F 13/15577* (2013.01); *A61F 13/56* (2013.01);
(Continued)

(58) Field of Classification Search
CPC .. A61F 13/622; A61F 13/15577; A61F 13/56; A61F 13/5622; A61F 13/5633;
(Continued)

(56) References Cited

U.S. PATENT DOCUMENTS 5,399,219 A * 3/1995 Roessler .......... A61F 13/15756
156/229
6,030,373 A * 2/2000 VanGompel ............ A61F 13/58
24/442

(Continued)

FOREIGN PATENT DOCUMENTS

EP 2835124 2/2015
JP 2003-159279 6/2003
(Continued)

OTHER PUBLICATIONS

International Search Report for PCT International Application No. PCT/US2015/025260, dated Jul. 1, 2015, 4 pages.
EP Search Report, EP 15780696, dated Oct. 20, 2017, 10 pages.

*Primary Examiner* — Jacqueline F Stephens

(57) ABSTRACT

A fixing member including a sheet-like base member 21 and a surface fastener 30 provided on the base member 21 is disclosed. The surface fastener 30 covers a surface of the base member 21 at a position separated from a tip end 21E1 of the base member 21 in a wrap-around direction, and minimum bending stiffness of the fixing member 20 as determined via a bending test using a Gurley tester being 150 mgf or less when measured using a test piece cut from a portion where the surface fastener 30 is provided. The surface S1 on the surface fastener 30 side of the portion 21a
(Continued)

on the tip end 21E1 side of the surface fastener 30 of the base member 21 is a surface with reduced engagement with the surface fastener 30.

10 Claims, 32 Drawing Sheets

(51) Int. Cl.
 *A61F 13/56* (2006.01)
 *A61F 13/68* (2006.01)

(52) U.S. Cl.
 CPC ......... *A61F 13/565* (2013.01); *A61F 13/5622* (2013.01); *A61F 13/5633* (2013.01); *A61F 13/5638* (2013.01); *A61F 13/5644* (2013.01); *A61F 13/62* (2013.01); *A61F 13/625* (2013.01); *A61F 13/627* (2013.01); *A61F 13/68* (2013.01)

(58) Field of Classification Search
 CPC .............. A61F 13/5638; A61F 13/5644; A61F 13/565; A61F 13/62; A61F 13/625; A61F 13/627; A61F 13/68
 USPC .......................... 604/386, 387, 391, 394, 396
 See application file for complete search history.

(56) References Cited

U.S. PATENT DOCUMENTS

| | | | |
|---|---|---|---|
| 6,231,557 | B1 | 5/2001 | Krautkramer |
| 6,323,388 | B1 | 11/2001 | Melius |
| 6,461,715 | B1 | 10/2002 | Guenther |
| 7,578,813 | B2 | 8/2009 | Mitsui |
| 7,855,314 | B2 | 12/2010 | Hanao et al. |
| 9,333,123 | B2 | 5/2016 | Otsubo et al. |
| 2001/0053905 | A1 | 12/2001 | Shingu |
| 2002/0138064 | A1 | 9/2002 | Datta |
| 2003/0100878 | A1* | 5/2003 | Leak ..................... A61F 13/622 604/386 |
| 2004/0243091 | A1 | 12/2004 | Mitsui |
| 2007/0286976 | A1 | 12/2007 | Selen |
| 2008/0086106 | A1 | 4/2008 | Karami |
| 2008/0097368 | A1 | 4/2008 | Molander |
| 2010/0191211 | A1* | 7/2010 | Molander ............. A61F 13/581 604/385.23 |
| 2011/0313389 | A1 | 12/2011 | Wood |
| 2012/0249744 | A1 | 10/2012 | Pesach et al. |

FOREIGN PATENT DOCUMENTS

| | | |
|---|---|---|
| JP | 2003-275245 | 9/2003 |
| JP | 2005-312707 | 11/2005 |
| JP | 2006-192112 | 7/2006 |
| JP | 2009-261824 | 11/2009 |
| WO | WO 2006-062810 | 6/2006 |
| WO | WO 2012112768 | 8/2012 |

* cited by examiner

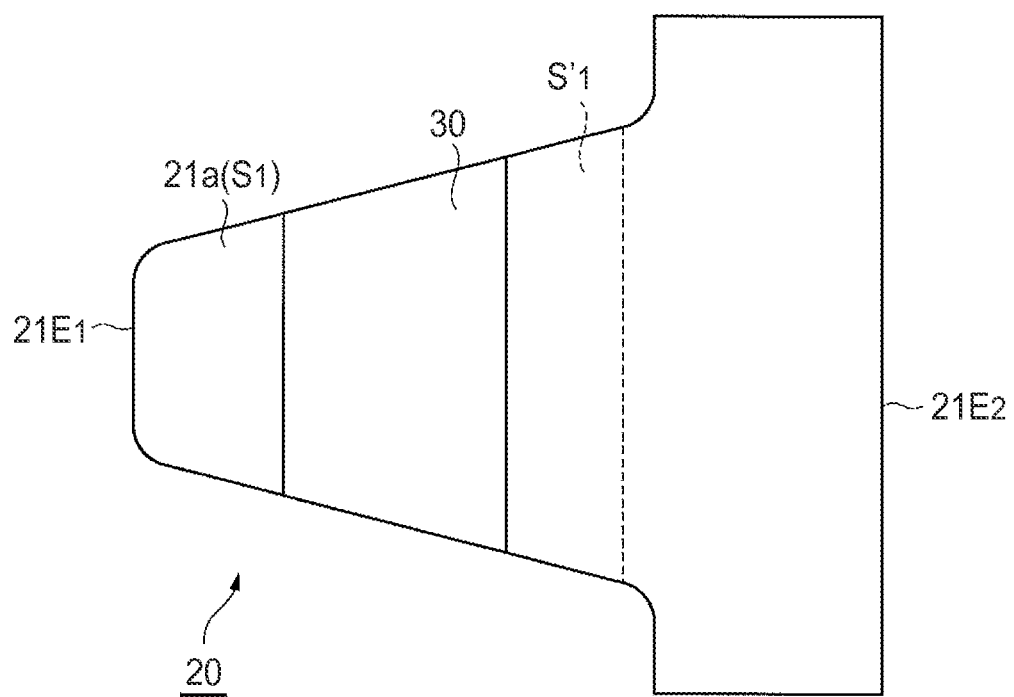
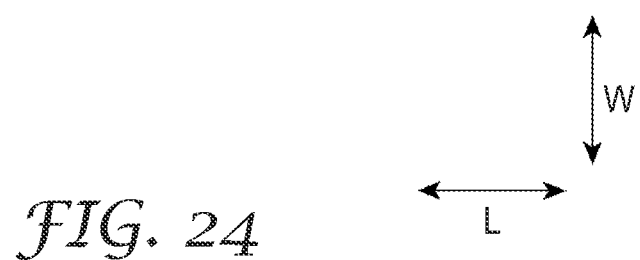
FIG. 24

FIXING MEMBER AND ABSORBENT ARTICLE

CROSS REFERENCE TO RELATED APPLICATIONS

This application is a national stage filing under 35 U.S.C. 371 of PCT/US2015/Apr. 10, 2015, filed Apr. 10, 2015, which claims the benefit of JP Application No. 2014-082995, filed Apr. 14, 2014, the disclosure of which is incorporated by reference in its/their entirety herein.

FIELD

One aspect of the present invention relates to a fixing member and an absorbent article.

BACKGROUND

Surface fasteners have been conventionally used for fixing different regions in a member to be fixed such as fabric, for fixing to each other a plurality of members to be fixed, and so on.

The disposable diaper disclosed in Japanese Unexamined Patent Application Publication No. 2003-159279 includes a diaper body in which an absorbent member is enclosed by a liquid permeable top sheet and a liquid impermeable back sheet, and fastening tapes fixed to the two respective sides of the rear of the diaper body. A male member is provided on the base material surface of each of the fastening tapes, and a female member of a fastening sheet is provided at the abdomen position on the rear surface of the back sheet. In this disposable diaper, the peeling force between the base material surface of the fastening tape and the male member is reduced, so that the two do not engage with each other.

The disposable diaper disclosed in Japanese Unexamined Patent Application Publication No. 2002-000649 includes wing parts formed from nonwoven fabric and which extend in a girth direction. A fastener portion is formed is formed on the outside edge of the wing parts by extending a portion of the nonwoven fabric in the girth direction, and the male member of a mechanical fastener is fitted to the inner surface of the fastener portion. A plurality of fine fused portions in which fiber is fused is formed on the inner surface of the wing parts, the number of fused parts formed per unit area on the inner surface is larger in the fastener portion and a first area near the fastener portion, and smaller in a second area inward of the first area.

SUMMARY

The fixing member used for fixing the member to be fixed includes, for example, a male member (hook member or the like) as a surface fastener, and the member to be fixed is fixed by connecting the surfaces of the male member and a female member to be engaged with the male member. In order to increase the stability of the fixing member for preventing displacement, it is effective to increase the dimensions of the surface fastener.

However, if the dimensions of the surface fastener increase, the ability to follow the movements of the member to be fixed tends to degrade. In the fixing member, the fixing member fixed to the member to be fixed can flexibly deform in response to the bending, twisting or the like of the member to be fixed by reducing the stiffness of the surface fastener. As a result, the ability to follow the movement of a member to be fixed can be reliably ensured even if the dimensions in both the width direction and the wrap-around direction of the surface fastener are adequately provided in order to increase stability for preventing the displacement.

If the stiffness of the surface fastener portion is small, however, the tip end of the fixing member can be easily and inadvertently folded back when the fixing member is used. In this case, the folded back portion remains folded back when the fixing member surface fastener is engaged, which hinders the use of the fixing member. The tip end of the fixing member is frequently the part that the user grips when attaching or detaching the fixing member, so it is inconvenient if this part remains folded back.

Therefore, for fixing members having surface fasteners, it is desirable to improve the stability for preventing the displacement between the fixing member and the member to be fixed, and the ability to follow the movements of the member to be fixed, while preventing the fixing member from being folded back during use.

One aspect of the present invention relates to a fixing member that includes a sheet-like base member and a surface fastener provided on the base member. The surface fastener of the fixing member according to one aspect of the present invention covers a surface of the base member at a position separated from a tip end of the base member. Bending stiffness from a bending test using a Gurley tested of the fixing member according to one aspect is a minimum of 150 mgf or less. The bending test is performed using a strip-shaped test piece cut from a portion where the surface fastener is provided by anchoring an end of the test piece using a clamp so that a length from a fixed end of the test piece to a free end thereof is 19.05 mm. Furthermore, in the fixing member according to one aspect, engagement with the surface fastener is reduced on a surface of the base member on a side on which the surface fastener is provided on a portion of the base member on the tip end side of the surface fastener.

According to this type of configuration, by making the stiffness of the portion where the surface fastener is provided low, the fixing member that is fixed to the member to be fixed can deform flexibly in accordance with the bending, twisting or the like of the member to be fixed. As a result, the ability to follow the movement of a member to be fixed can be reliably ensured, even if the dimensions of the surface fastener are adequately provided in order to increase stability for preventing displacement. In addition, because the stiffness of the portion where the surface fastener is provided is low, although the tip end portion of the fixing member tends to easily fold back, in that case the base member surface that contacts the surface fastener is a surface with reduced engagement with the surface fastener, so the tip end portion of the fixing member does not easily remain folded back.

The surface with reduced engagement with the surface fastener may have a maximum value of 90-degree peeling strength with respect to the surface fastener of 0.10 N/15 mm or less. Furthermore, the surface with the reduced engagement with the surface fastener may be the surface of a fiber assembly that has been heat treated.

In addition, the bending stiffness of the fixing member by a bending test using a Gurley tester according to another aspect is 30 mgf or less. Here, the bending test is performed using a strip-shaped test piece cut from a portion extending from the portion where the surface fastener is provided to a portion at the tip end side where the surface fastener is not provided, by anchoring the end of the test piece where the surface fastener is not provided using a clamp so that the length from the fixed end of the test piece to the free end thereof is 19.05 mm, and the minimum value of the length from the fixed end to the portion of the test piece where the surface fastener is provided is 3.65 mm.

In a fixing member according to yet another aspect, the portion of the base member on the tip end side of the surface fastener may be folded back.

An absorbent article according to one configuration of the present invention includes any of the above fixing members.

Another aspect of the present invention relates to a method of manufacturing a fixing member according to the above aspects. A method according to one aspect includes a step of heat treating a portion of the base member on the surface fastener side so as to reduce engagement with the surface fastener, and the heat treated surface is the surface of a fiber assembly.

According to this aspect, for the fixing members obtained, the stability for preventing displacement between the fixing member and the member to be fixed, and, the ability to follow the movements of the member to be fixed can be improved, while preventing the tip end portion of the fixing member from being unintentionally folded back during use.

A method according to another aspect may also include a step of preparing a long raw material base material that will form a plurality of base members; a step of fitting the surface fastener to a region separated from the position corresponding to the tip end of the base member; and a step of dividing the laminate that includes the raw material base material and the surface fastener provided on the raw material base material into a plurality of fixing members. In this case, the step of heat treating the portion of the surface of the base member on the surface fastener side so as to reduce engagement with the surface fastener may be a step of heat treating the surface of the raw material base material between a region where the surface fastener is fitted and a position corresponding to the tip end of the base member so as to reduce the engagement with the surface fastener.

In a method according to yet another aspect, the step of fixing the surface fastener to the surface of the raw material base material may be performed by heating the region of the surface of the raw material base material to which the surface fastener is attached. In this case, the step of fixing the surface fastener and the step of heat treating the portion of the surface of the base member on the surface fastener side so as to reduce engagement with the surface fastener may be simultaneously carried out by continuously heating the region on the surface of the raw material base material where the surface fastener is fixed and the region between the region where the surface fastener is fixed and the position corresponding to the tip end of the base member while moving the raw material base material in a longitudinal direction thereof.

In a method according to yet another aspect, the step of dividing the laminate into the plurality of the fixing members may include dividing the laminate in the width direction along the longitudinal direction of the laminate along a winding line that periodically winds and includes ridge portions that include portions that will become the tip end, and dividing each divided piece in the longitudinal direction thereof at positions corresponding to valley portions of the winding line.

According to one aspect of the present invention, in relation to the fixing member including the surface fastener, it is possible to improve stability for preventing displacement between the fixing member and the member to be fixed and the ability to follow the movements of the member to be fixed and to prevent the fixing member from being folded back during use. Furthermore, according to one aspect of the present invention, it is possible to reduce the irritation of the skin of the wearer of an absorbent article or clothing, when the fixing member is fitted to the member to be fixed of the absorbent article or clothing or the like.

BRIEF DESCRIPTION OF THE DRAWINGS

FIG. 24 shows another example of a fixing member.

DETAILED DESCRIPTION

The term 'fixing member' in the present specification refers to a member that includes a base member and a surface fastener provided on this base member, and that is used to fix a member to be fixed. For example, a fixing member described in the present specification can be used in applications such as (1) connecting together a first region and a second region in a member to be fixed (article) (more specifically, linkage between a front waist part and a rear waist part in a disposable diaper or another absorbent article, fixing left and right frontal areas, collars, and/or cuffs, or the like in clothing, and fixing the opening of the upper part of a shoe), (2) fixing a plurality of different members to be fixed to each other (more specifically, fixing and attachment of an absorbent article such as a sanitary pad or another sanitary product to clothing), and (3) fixing a member to be fixed by wrapping the fixing member around the member to be fixed, and engaging a surface fastener with a base member (to limit movement) (more specifically, to maintain the shape of an article folded or rolled up into a small form, to prevent displacement and peeling of a wet compress or the like affixed to the skin). However, the range encompassed by the term is not limited thereto.

The term 'surface fastener' in the present specification refers to a sheet-like member that can be removably fixed to the member to be fixed, thereby engaging the surface thereof with the surface of the member to be fixed. A representative example of a surface fastener male member is a hook member, to be described later, that engages with fiber or the like that constitutes the surface of the member to be fixed, so that the two surfaces can be coupled to each other. However, the range encompassed by the term 'surface fastener' is not limited thereto. For example, the surface fastener is a concept that also includes a female member such as a loop member.

Embodiments of the present invention will now be described in detail with reference to the attached drawings. Note that in the descriptions of the drawings, the same or equivalent elements are assigned identical reference numbers and are not repeatedly described.

Figure 1:
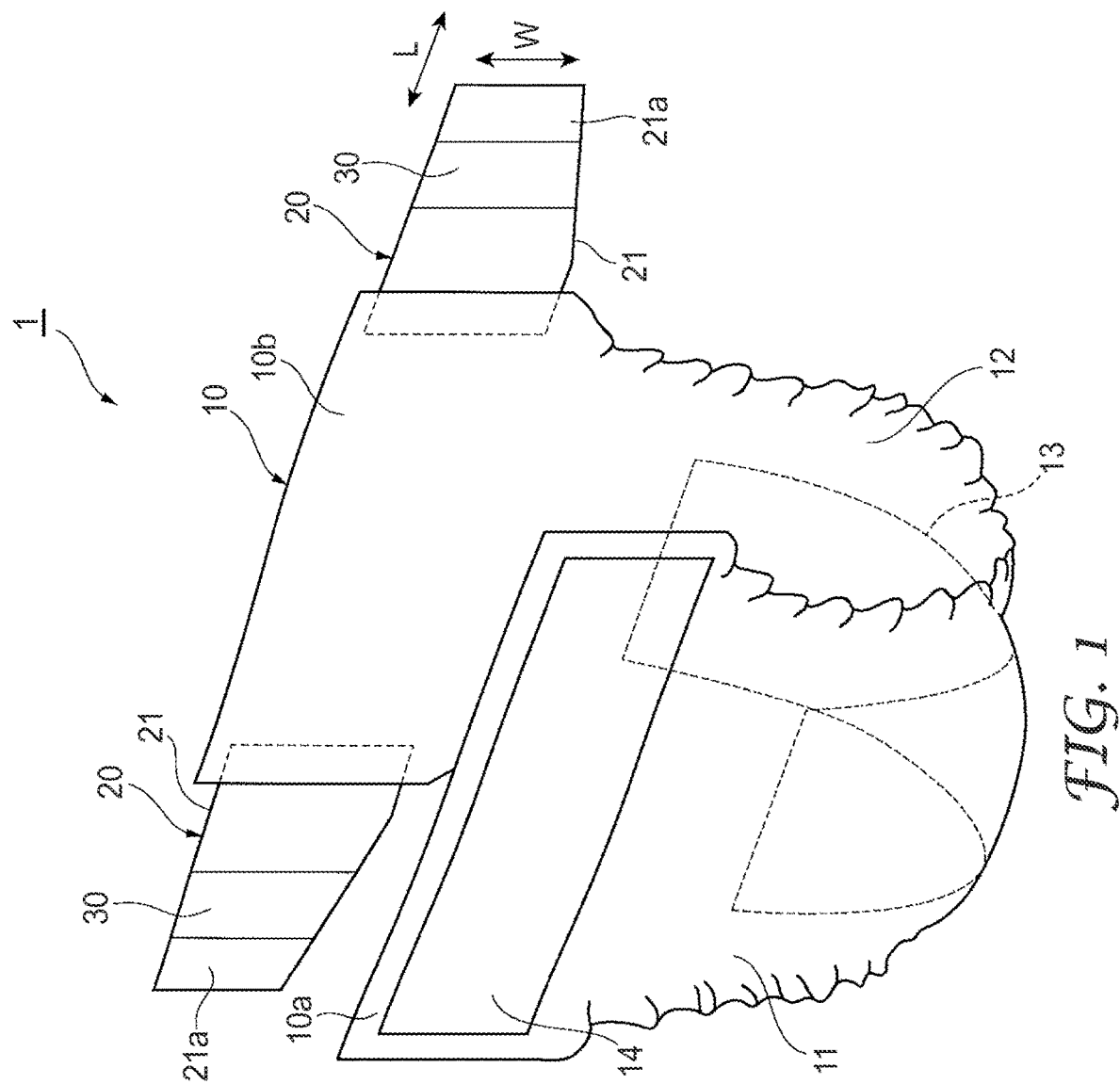
FIG. 1 is a perspective view of a diaper with a fixing member according to an embodiment.
Figure 2:
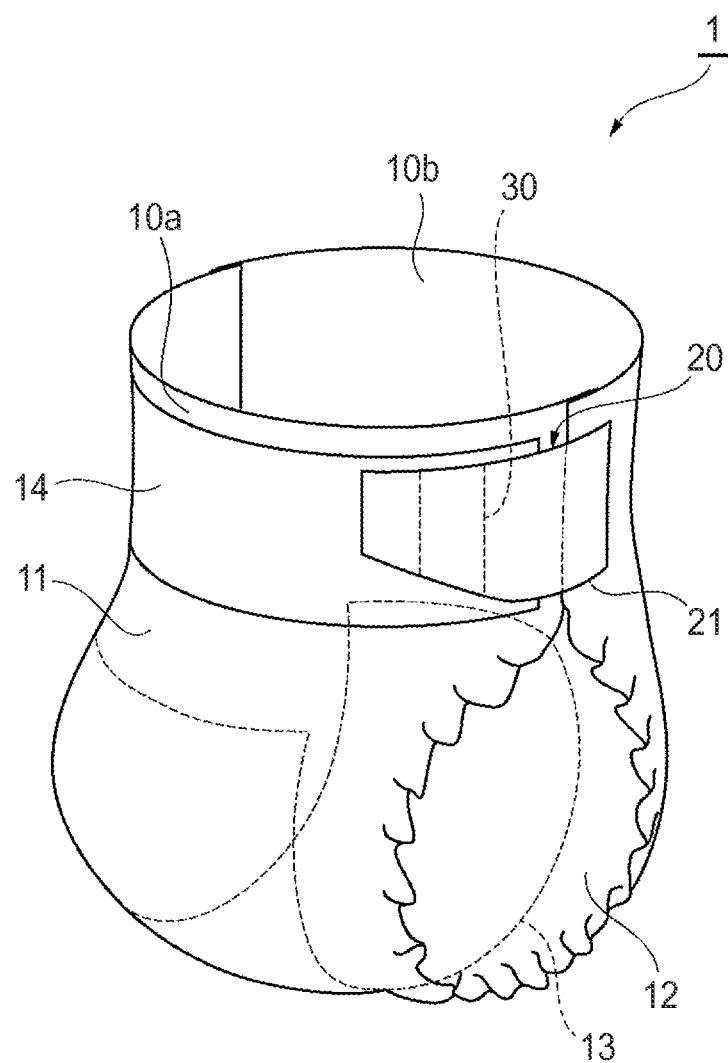
FIG. 2 is a perspective view showing a state in which the diaper of FIG. 1 is being worn.

As shown in FIGS. 1 and 2, in the embodiments, a fixing member 20 is described while referring to an example that applies to an absorbent article 1. In FIGS. 1 and 2, an open-type (flat-type) diaper is given as an example of the absorbent article 1, however, the absorbent article provided with the fixing member is not limited to the diaper shown in FIGS. 1 and 2, and examples thereof can include diapers of other configurations such as a tape-fastened type diaper and a pad type diaper, and sanitary pads, sanitary pads integrated with shorts as well as other menstrual sanitary products and sanitary articles.

The diaper (absorbent article) 1 includes a sheet-shaped main body part 10 that covers the crotch area of a wearer from an abdominal side to a back side, and a pair of fixing members 20 that detachably connect an abdominal end part 10a and a back end part 10b of the main body part 10 at left and right sides of the waist of the wearer. In the present specification, a surface of the diaper 1 on the wearer's side is referred to as 'inner surface', and an opposite surface is referred to as the 'outer surface'.

The main body part 10 includes an outside sheet 11, a liquid permeable inside sheet 12 laminated to the interior side of the outside sheet 11, and a liquid absorbent polymer absorbent body 13 contained between the outside sheet 11 and the inside sheet 12. The outside sheet 11 is typically configured by a laminate of a liquid impermeable film with a nonwoven fabric layer, and the liquid impermeable film is disposed on the polymer absorbent body 13 side while the nonwoven fabric layer is disposed on the outer surface of the body of the diaper 1. In other words, when the wearer wears the diaper 1, the inside sheet 12 is disposed on the inner surface side of the body of the diaper 1 adjacent to the skin of the wearer while the outside sheet 11 (the nonwoven fabric layer thereof) is disposed on the outer surface of the body of the diaper 1 adjacent to the clothing or the like of the wearer. For example, a polypropylene nonwoven fabric produced using the spunbond method can be used as the nonwoven layer used in the outside sheet 11. In this case, the nonwoven layer thereof can be used for fixing to the fixing member.

Note that a belt-shaped loop member 14 that extends in a width direction of the main body part 10 (lateral direction when the wearer wears the diaper) may also be provided on the outer surface of the abdominal end part 10a of the main body part 10. The loop member is typically configured by a knitted fabric, a sheet, or a nonwoven fabric, or a combination of two or more of these, and includes a plurality of fibers and loops with which hooks engage. Furthermore, instead of providing the loop member 14, the outside sheet 11 having an outer surface layer that includes a plurality of loops with which hooks engage may be used, or as discussed above, the outside sheet 11 may be configured by the nonwoven fabric or the like which enables the hooks to engage with the fibers thereof.

As shown in FIG. 1, in the present embodiment, each of the fixing members 20 is provided with a base member 21 and a surface fastener 30. In the present specification, a surface on the surface fastener side of the base member 21 is referred to as 'inner surface', and a rear surface is referred to as 'outer surface'. The paired fixing members 20 are fixed to two ends of the back end part 10b in a width direction of the main body part 10 so as to project outward along the width direction from the back end part 10b. The base end side (main body part 10-side) of the base member 21 is attached to an outer surface of the back end part 10b by adhesive bonding, sewing, welding, or the like. As shown in FIG. 2, the fixing members 20 connect the abdominal end part 10a to the back end part 10b when the wearer wears the diaper 1, by engaging the surface fastener 30 with the loop member 14 in a state of wrapping the base member 21 around the abdominal end part 10a with the surface fastener 30 on the inner side. The wearer can thereby wear the diaper 1.

In the present specification, as shown in several drawings, the direction in which the fixing members 20 are wrapped around the member to be fixed (the main body part 10 in the example of FIG. 1) (hereafter, often 'wrap-around direction') is indicated by symbol L, and a direction orthogonal to the wrap-around direction L is defined as the width direction W. The wrap-around direction L is the same as the direction in which the base member 21 projects from the main body part 10.

Figure 3:
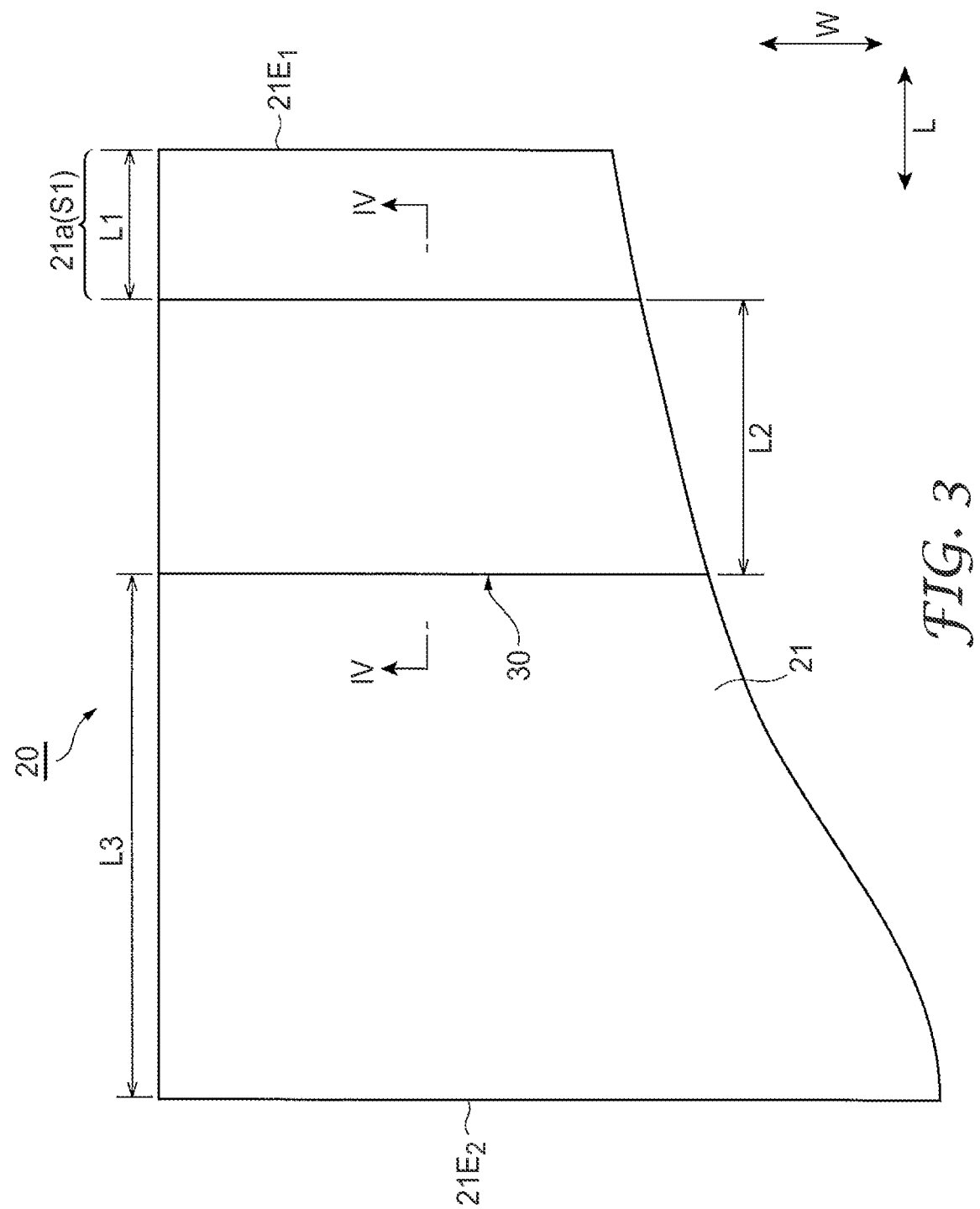
FIG. 3 shows an example of a fixing member.
Figure 4:
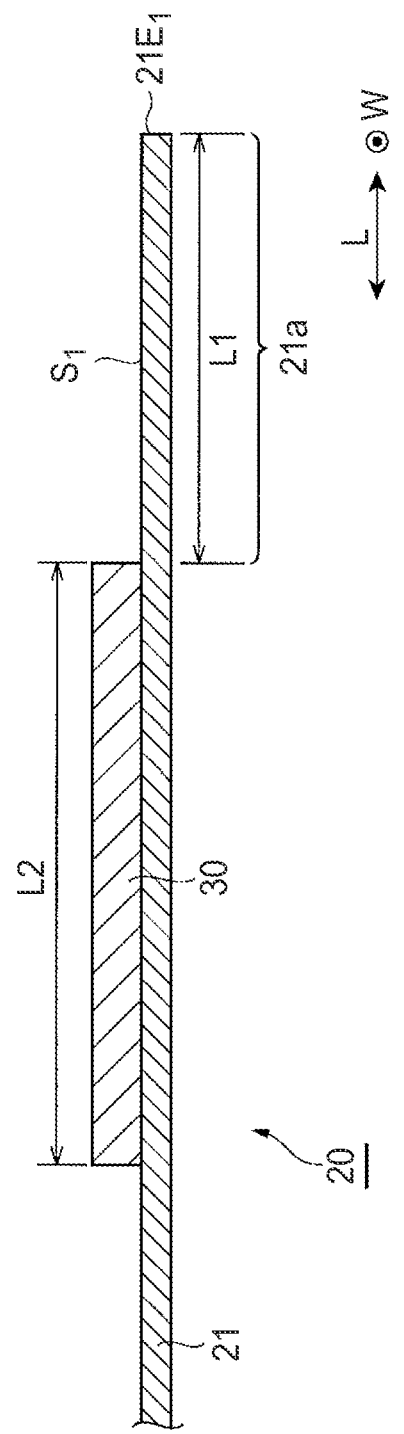
FIG. 4 is a cross-sectional view taken along a line IV-IV of FIG. 3.

FIG. 3 shows an example of the fixing member. FIG. 4 is a cross-sectional view taken along a line IV-IV of FIG. 3. The base member 21 of the fixing member 20 shown in FIGS. 3 and 4 extends along the width direction of the main body part 10 (wrap-around direction of the fixing member 20) L.

In the present specification, "extend" means to have a shape that extends along a certain direction. While the base member 21 extends along the wrap-around direction L of the fixing member 20, the base member 21 may also include parts that extend along other directions. For example, the end portion of the body part side of the base member 21 may project in the width direction W, and in this case, it can be said that the end portion of the base member 21 extends partially along the width direction.

In a case of the fixing member 20 of FIG. 3, the base member 21 has a wing shape extending along the wrap-around direction L, and includes a tip end $21E_1$ in the wrap-around direction L, and a base end $21E_2$ opposite to the tip end $21E_1$. In the present specification, 'tip end' refers to the end of a member in an extension direction of the member. The tip end of the base member is not necessarily straight, but may be curved or may be of a shape of a combination of straight and curved shapes. An end portion on one base end $21E_2$ side of the base member 21 extends along the width direction W. In other words, the base member 21 has a portion that extends in the width direction W at the end on the base end $21E_2$ side. In the present specification, the shape when the width of the tip end $21E_1$ and the base end $21E_2$ are different is also categorized as a belt shape.

The size (overall area) of the base member 21 may be selected as appropriate from the point of view of the ability of the base member 21 to follow the member to be fixed. For example, the maximum length of the base member 21 in the wrap-around direction L may be not less than 60 mm, and not more than 300 mm or not more than 250 mm. The maximum width in the width direction W of the base member 21 may be 40 mm or more, and may be 200 mm or less or 150 mm or less.

In the fixing member 20 shown in FIGS. 3 and 4, the surface fastener 30 is disposed in a position at a distance L1 from the tip end $21E_1$ of the base member 21. The surface fastener 30 has a constant width L2 in the wrap-around direction L. The portion (tip end of the base member) 21a of the base member 21 on the tip end $21E_1$ side of the surface fastener 30 can function as a grip that the user grips to attach/detach the surface fastener 30. A ratio of the width L2 if the surface fastener 30 to a maximum length in the wrap-around direction L may be, for example, not less than 0.5 or not less than 0.1, and not more than 0.9 or not more than 0.7. Furthermore, the width L2 of the surface fastener 30 may be not less than 5 mm or not less than 10 mm, and not more than 100 mm or not more than 80 mm.

The (maximum) distance between the tip end $21E_1$ of the base member 21 and the surface fastener 30, i.e., the maximum length L1 in the wrap-around direction L of the grip, as shown in FIG. 3, may be greater or may be less than the (maximum) distance L3 on the base member 21 between the base end $21E_2$ and the surface fastener 30. For example, L1/L3 may be not less than 0.01 or not less than 0.03, and may be not more than 2 or not more than 1. L1 may be not less than 1 mm or not less than 2 mm, and not more than 30 mm or not more than 20 mm.

In the fixing member 20, particularly if the portion where the surface fastener 30 is provided is flexible, there is the advantage of stability for preventing displacement between the fixing member and the member to be fixed and the ability to follow the movements of the member to be fixed. Specifically, the bending stiffness of the fixing member 20 in a bending test using a Gurley testing machine may be not more than 150 mgf. In this case, the bending test is performed using a strip-shaped test piece cut from a part where the surface fastener 30 is provided, and one end of the test piece is fixed with a clamp so that a length from a fixed end to a free end of the test piece is 19.05 mm. This minimum bending stiffness may be not more than 120 mgf or not more than 100 mgf. Furthermore, this minimum bending stiffness may be not less than 5 mgf or not less than 10 mgf.

In the present specification, the term 'bending stiffness' means the bending stiffness measured in a bending test on a cantilever beam using a Gurley testing machine, in accordance with the method prescribed in TAPPIT 543 om-11. The bending stiffness measured according to this method is sometimes referred to as "Gurley stiffness" by persons skilled in the art. The bending stiffness is measured in an environment of a temperature of 23° C. and a relative humidity of 50%.

Figure 26:
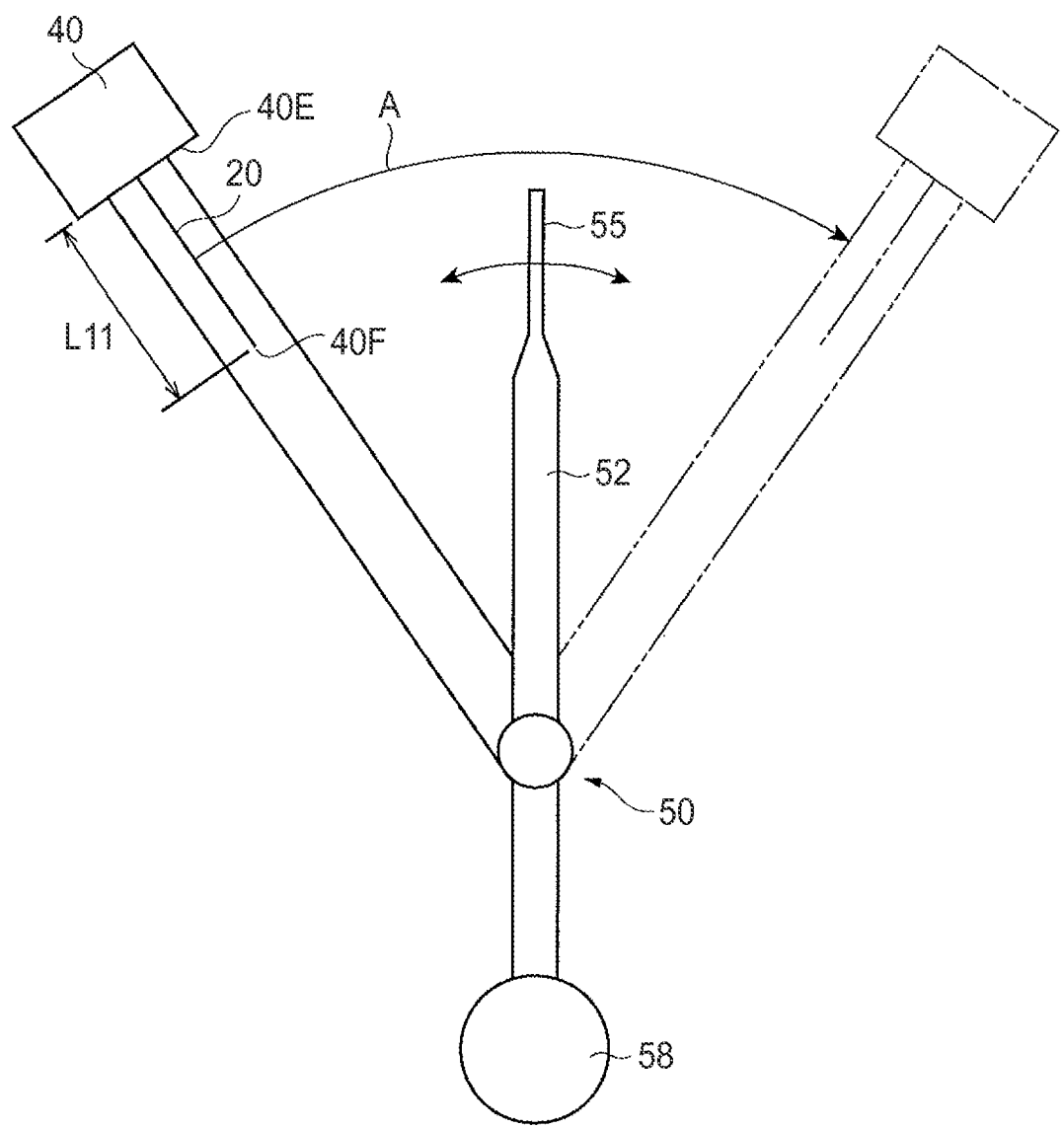
FIG. 26 shows an example of method of measurement of the bending stiffness of the fixing member.

FIG. 26 shows the bending test method to measure the bending stiffness (Gurley stiffness). As shown in FIG. 26, one end of the fixing member 20 as the test piece is gripped by a clamp 40. By rotating the clamp 40 about a rotating shaft 50, the fixing member 20 moves along a direction A about the rotating shaft 50. A plate-like member 55 is provided at one tip end of a pendulum shaft 52 rotatably provided about the rotating shaft (support point) 50, and a weight 58 is fitted to the shaft 52. A mass and an attachment position of the weight 58 are selected as appropriate in accordance with the degree of the bending stiffness of the fixing member 20.

When the fixing member 20 moves in the circumferential direction A (clockwise) at a constant speed, the end portion of the free end 40F side of the fixing member 20 strikes against the plate-like member 55 and the fixing member 20 is thereby bent. When the fixing member 20 continues to move, the plate-like member 55 is released from the fixing member 20 after being pushed by the fixing member 20 and rotating to a certain extent. The bending stiffness is obtained based on a load received by the plate-like member 55 in this process. Thereafter, by moving the fixing member 20 in an opposite direction (counterclockwise), the bending stiffness when the fixing member 20 is bent in the opposite direction can be measured. The speed of movement of the test piece is set to one reciprocation per minute. The bending stiffness is obtained as the average value of two measured values obtained when the test piece reciprocates once circumferentially.

A length (length of the cantilevered test piece) L11 of the fixing member 20 from the end (fixed end) 40E of the clamp 40 to the free end 40F is set to 19.05 mm (0.75 inches). In the present specification, 'fixed end' means the end portion of the test piece closer to the clamp from among the portions of the test piece that are not gripped by the clamp. Normally 'fixed end' coincides with the end of the clamp. 'Free end' means the tip end of the cantilevered test piece opposite to the fixed end of the test piece.

Figure 27:
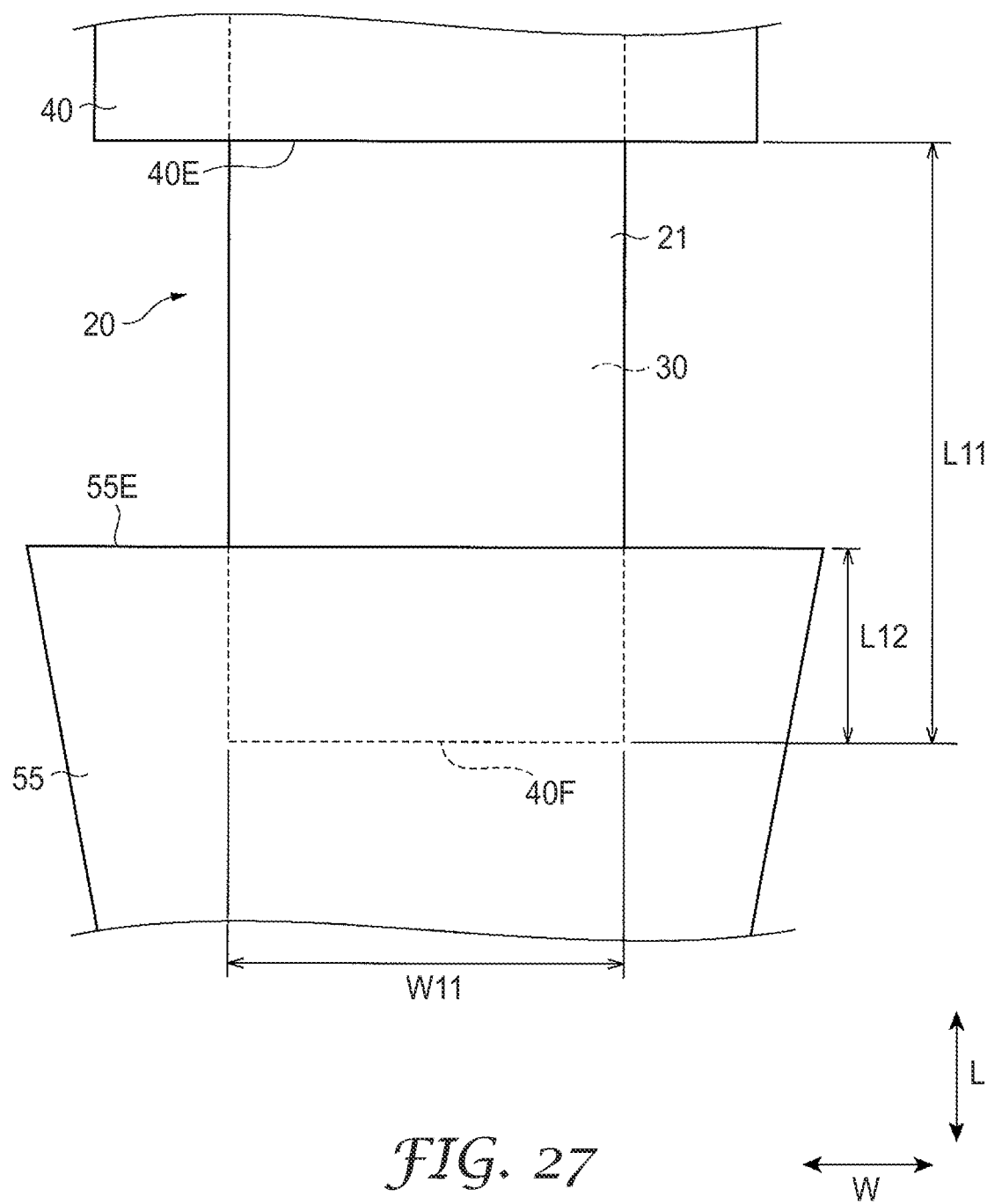
FIG. 27 shows an example of method of measurement of the bending stiffness of the fixing member.

FIG. 27 shows the fixing position of the test piece for the bending test. The fixing member 20 serving as the test piece is a strip-shaped test piece that is the laminate of the base member 21 and the surface fastener 30. A longitudinal direction of the test piece is selected so that the bending stiffness of the portion of the fixing member 20 where the surface fastener 30 is provided is a minimum. In other words, in the present specification "the minimum bending stiffness is not more than 150 mgf" means that the bending stiffness measured using the test piece whose longitudinal direction is the direction with the minimum bending stiffness from among the in-plane directions of the surface fastener 30 is not more than 150 mgf. If the surface fastener has isotropic properties in-plane, the longitudinal direction of the test piece can be selected as desired, and even if the surface fastener is anisotripic, normally a person skilled in the art will understand in which direction the minimum bending stiffness is measured.

The front/reverse orientations of the test piece (fixing member 20) that is gripped may be selected as desired. The length (width) W11 in the width direction W orthogonal to the wrap-around direction L of the test piece (fixing member 20) is 25.4±0.4 mm (1±1/64 inches) or 12.7±0.4 mm (0.5±1/64 inches). An overall length in the wrap-around direction L of the test piece (fixing member 20) may be, for example, about 25.4 mm (1 inch) so that the portion to be gripped by the clamp 40 is ensured. In the portion of the test piece (fixing member 20) with a length L12 from the free end 40F, the plate-like member 55 is applied. L12 is set to 6.35±0.4 mm (0.25±1/64 inches).

In the fixing member 20, if the portion near the surface fastener 30 is flexible, there is the advantage of stability for preventing displacement between the fixing member and the member to be fixed, and the ability to follow the movements of the member to be fixed. Specifically, the bending stiffness of the fixing member 20 in the bending test using the Gurley testing machine may be not more than 30 mgf. In this case, the bending test is performed using a strip-shaped test piece cut from a portion extending from the portion where the surface fastener 30 is provided to a portion at the tip end $21E_1$ side where the surface fastener 30 is not provided, the end of the test piece on the portion where the surface fastener 30 is not provided is fixed to the clamp so that the length of the test piece from the fixed end to the free end is 19.05 mm, and, the minimum value of the length of the portion of the test piece where the surface fastener 30 is not provided is 3.65 mm, and the bending stiffness may be not more than 25 mgf or not more than 20 mgf. Furthermore, the bending stiffness may be not less than 1 mgf or not less than 3 mgf.

Figure 28:
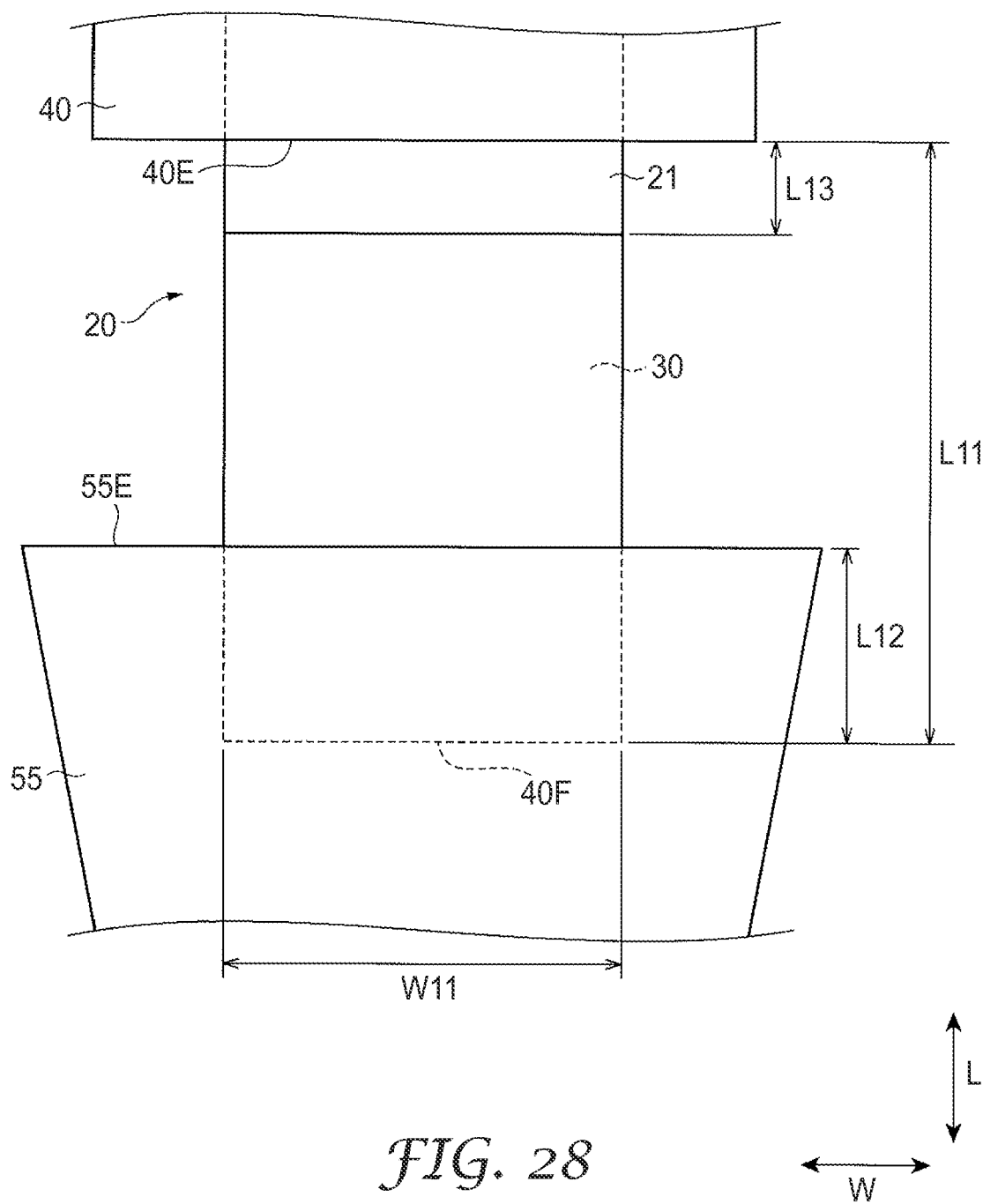
FIG. 28 shows an example of method of measurement of the bending stiffness of the fixing member.

This bending stiffness is also measured in the same way as for the bending test as described above using the test piece cut from the portion where the surface fastener is provided, apart from the part from which the test piece is cut and the method of fixing the test piece. FIG. 28 shows the fixing position of the test piece for the bending test. In the example of FIG. 28, the fixing member 20 as test piece is cut from the portion where the base material 21 and the surface fastener 30 are laminated to a portion on the tip end $21E_1$ side where the surface fastener 30 is not provided. One end of the test piece (fixing member 20) on the side of the portion where the surface fastener 30 is not provided (the base member 21 only portion) is gripped by the clamp 40. A length L13 of the test piece (fixing member 20) from the fixed end 40E to the portion where the surface fastener 30 is provided is set to a minimum of 3.65 mm. The longitudinal direction of the test piece is selected as desired so that the length L13 can be the minimum value of 3.65 mm. In the example in FIG. 28, the end 40E of the clamp and the edge portion on the clamp 40 side of the surface fastener 30 are parallel, but the edge portion may be inclined, or the edge portion may be curved. In any case, the test piece is gripped so that the length L13 is the minimum value of 3.65 mm. W11, L11, and L12 are set in the same way as for FIG. 26.

In the bending test as described above, the bending stiffness when the test piece is fixed at a position so that the length of the portion where the surface fastener 30 is not provided from the fixed end 40E exceeds the minimum value of 3.65 mm may be not more than 30 mgf, or may exceed 30 mgf. Particularly if the tip end portion of the grip portion 21a has the appropriate stiffness, it has advantages in terms of handling. As described later, the grip portion 21a can be given a certain amount of stiffness by folding back the tip end portion of the base member 21.

The fixing member having the bending stiffness as described above can be obtained by, for example, using the base material having flexibility as described later, or using various types of hook members as described later.

Refer back to FIGS. 3 and 4. The surface $S_1$ of the portion (grip portion) 21a on the tip end $21E_1$ side of the surface fastener 30 of the base member 21 is a surface on which engagement with the surface fastener 30 is reduced. Therefore, when the grip portion 21a is unintentionally folded back, the grip portion 21a does not easily remain attached to the surface fastener 30. In one aspect, the maximum value of the 90-degree peeling strength between the surface $S_1$ and the surface fastener 30 may be not more than 0.10 N/15 mm. The upper limit of the maximum value of the 90-degree peeling strength may be 0.09 N/15 mm or 0.08 N/15 mm. The maximum value of the 90-degree peeling strength may be substantially 0 N/15 mm.

In the present specification, "the maximum value of the 90-degree peeling strength between the surface $S_1$ of the base member and the surface fastener 30" means the maximum value of the peeling strength when the portion (grip portion) 21a on the tip end $21E_1$ side of the surface fastener 30 is cut from the fixing member 20, from the cut out grip portion 21a a rectangular base member-side test piece is cut out having a pair of sides in opposition to the wrap-around direction L, and with a length (width) W20 in the width direction W orthogonal to the wrap-around direction L of 15 mm, the surface $S_1$ of the test piece on the surface fastener 30 side is superimposed onto the surface fastener 30, and the peeling strength is measured by peeling the test piece at the speed 300 mm/minute in the direction of 90 degrees to the surface of the surface fastener 30 and the wrap-around direction L from the tip end $21E_1$ side. Superimposing the base member-side test piece on the surface fastener 30 is carried out by the method of applying a 500 gf load to the base member-side test piece in the direction perpendicular to the surface of the surface fastener 30, and at the same time applying a load of 500 gf in the wrap-around direction L to the base member-side test piece. If it is not possible to superimpose the base member-side test piece on the surface fastener and carry out the peeling test by this method, the maximum value of the 90-degree peeling strength is considered to be 0 N/15 mm. Measurement of the 90-degree peeling strength is carried out in the environment of a temperature of 23° C. and a relative humidity of 50%.

FIGS. 29, 30, 31, and 32 show the method of measuring the 90-degree peeling strength between the surface $S_1$ of the portion of the base member 21 on the tip end $21E_1$ side of the surface fastener 30 and the surface fastener 30.

Figure 29:
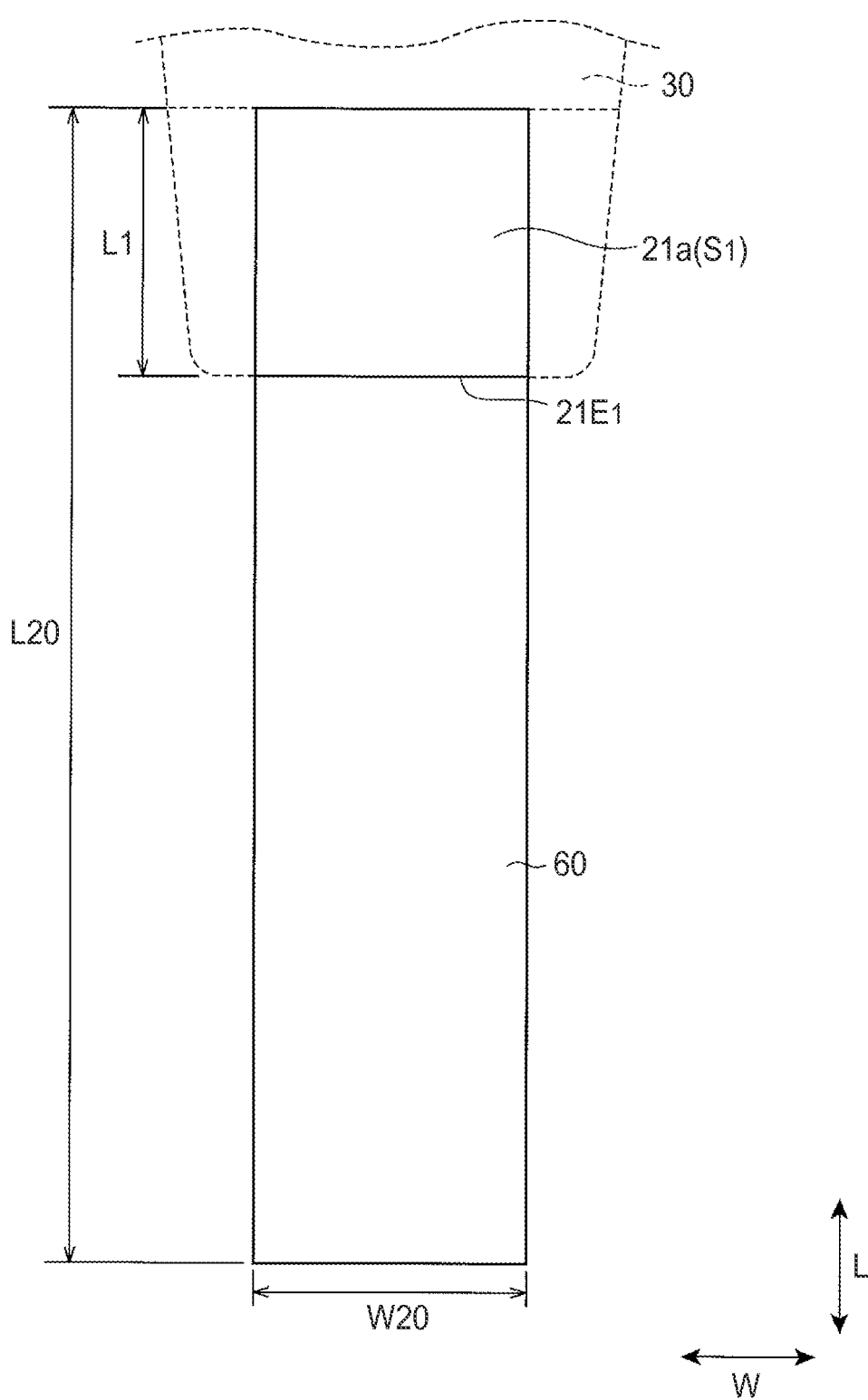
FIG. 29 shows an example of test piece on the base member side for measuring the 90-degree peeling strength between the surface of the base material and the surface fastener.

As shown in FIG. 29, a rectangular portion from the grip portion 21a having a pair of sides along the wrap-around direction L is used as the base member 21-side test piece. This test piece has the same length L1 as the grip portion 21a. The test piece width W20 is 15 mm. The end portions of a long and narrow strip of paper 60 having a length L20 and a width W20 are joined together via a double-sided adhesive tape. The length L20 of the strip of paper is, for example, 210 mm. In the present specification, the maximum value of the 90-degree peeling strength between the surface $S_1$ of the grip portion 21a and the surface fastener 30 is not more than 0.10 N/15 mm means the maximum value of 90-degree peeling strength is not more than 0.10 N/15 mm when the 90-degree peeling strength is measured between a test piece cut from an arbitrary position in the width direction W of the grip portion 21a (for example, the center portion in the width direction), having a width W20 of 15 mm, and that includes the whole grip portion 21a in the wrap-around direction L at that position, and the surface fastener 30.

Figure 30:
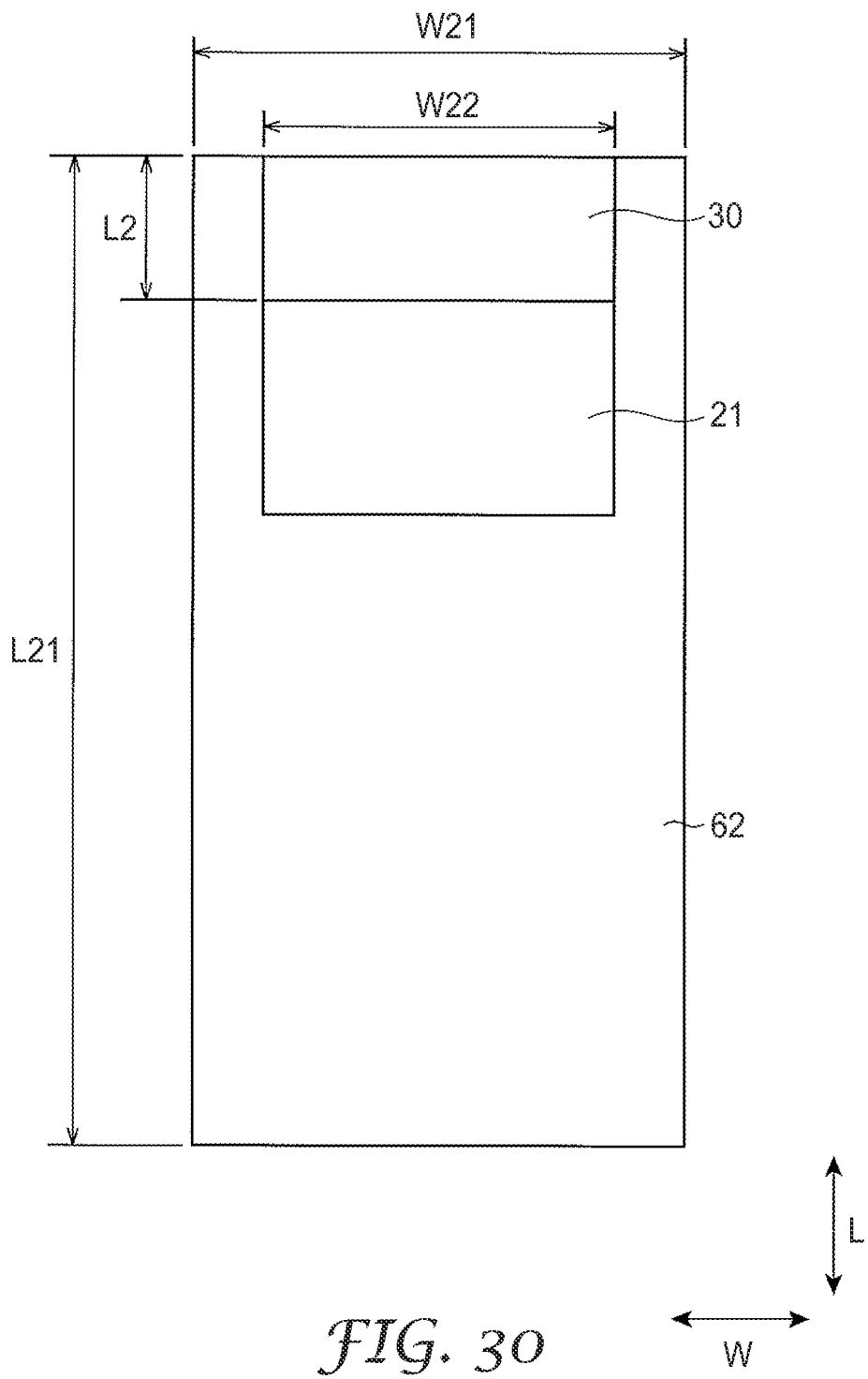
FIG. 30 shows an example of test piece on the surface fastener side for measuring the 90-degree peeling strength between the surface of the base member and the surface fastener.

As shown in FIG. 30, a portion from the portion where the surface fastener 30 is provided to a portion where the surface fastener 30 is not provided from the fixing member 20 is used as the surface fastener 30-side test piece. The length in the wrap-around direction L of the portion of the surface fastener 30-side test piece where the surface fastener 30 is provided may be the same as the width L2 of the surface fastener in the fixing member 20. If the length (the length of the base member-side test piece) L1 of the grip portion 21a is larger than the width L2 of the surface fastener, the 90-degree peeling strength is measured between the surface $S_1$ of a portion the length L2 from the tip end $21E_1$ in the grip portion 21a and the surface fastener 30. The surface fastener 30-side test piece is fixed to the center of an end portion of a panel (for example, a stainless steel panel) 62 having the length L21, width W21, and a smooth and flat surface, via the double-sided adhesive tape. The size and mass and so on of the panel 62 are set as desired.

Figure 31:
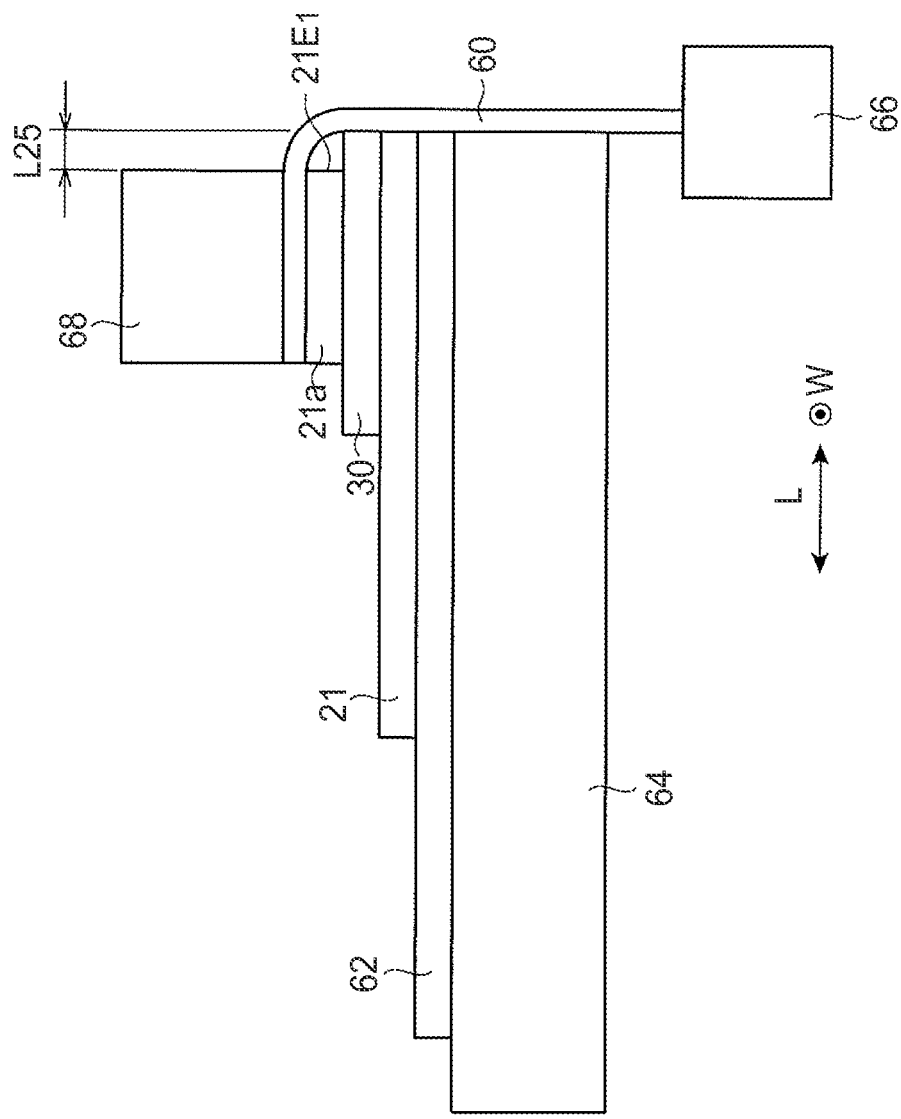
FIG. 31 shows an example of a method of measurement of the 90-degree peeling strength between the surface of the base member and the surface fastener.

Next, as shown in FIG. 31, the panel 62 is placed on a platform 64, and the base member-side test piece (grip portion 21a) is placed on the surface fastener 30. The distance L25 between the tip end $21E_1$ of the base member-side test piece (grip portion 21a) and the edge of the surface fastener 30 is set to an arbitrary value equal to or greater than 0. In this state, a weight 68 is placed on the base member-side test piece (grip portion 21a), and a load of 500 gf is applied in a direction perpendicular to the surface of the surface fastener 30 onto the whole base member-side test piece (grip portion 21a). In addition, a weight 66 is suspended from the end of the strip of paper 60 on the opposite side to the base member-side test piece (grip portion 21a), so that a load of 500 gf is applied to the base member-side test piece in the wrap-around direction L. Three seconds after the load is applied in the wrap-around direction L, the weights 66, 68 are removed.

Figure 32:
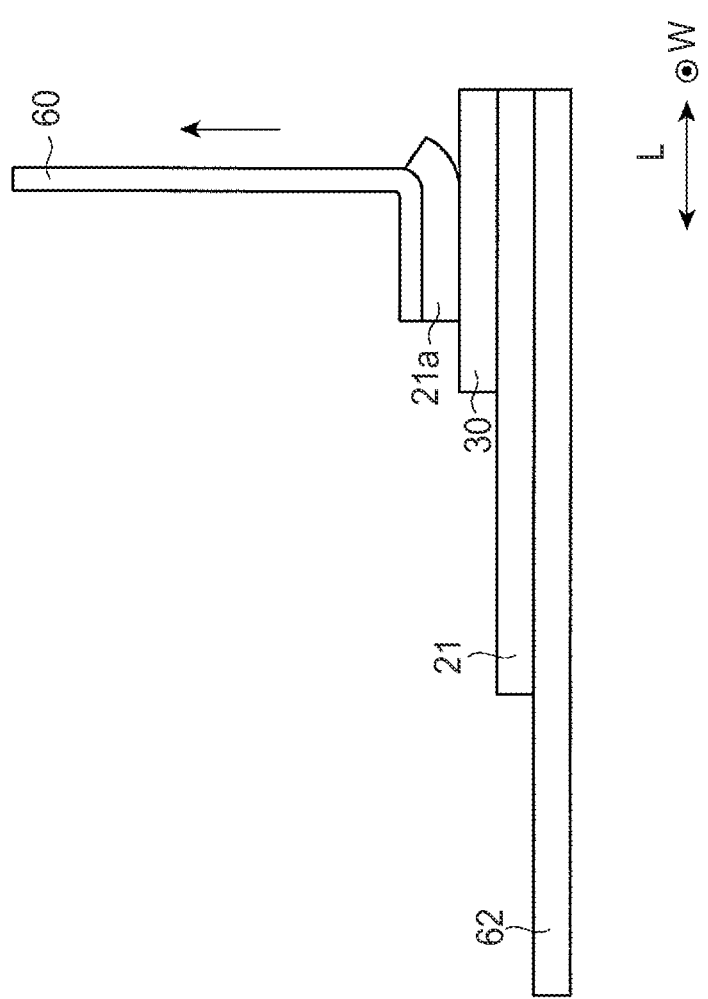
FIG. 32 shows an example of a method of measurement of the 90-degree peeling strength between the surface of the base member and the surface fastener.

Thereafter, as shown in FIG. 32, the test piece (grip portion 21a) is peeled by pulling up the strip of paper 60 in the direction perpendicular to the surface of the surface fastener 30 and the wrap-around direction L, and at this time, the peeling strength per 15 mm width of the base member-side test piece is measured. In this measurement, the maximum value of the 90-degree peeling strength is obtained in the process of peeling off the entire test piece (grip portion 21a).

If the surface of the base member 21 on the surface fastener 30 side is configured by a fiber assembly to be described later, the surface with reduced engagement with the surface fastener 30 can include a surface on which the fiber assembly has been heat treated. Alternatively, engagement with the surface fastener may be reduced by chemical treatment on the surface, or by providing another layer that has substantially no engagement with the surface fastener on the grip portion 21a by coating or laminating. In several aspects, the surface with reduced engagement with the surface fastener is introduced by a method so that the bending stiffness as described above measured using a test piece that includes the portion (grip portion 21a) on which the surface fastener 30 is not provided does not exceed 30 mgf.

The base member 21 may be a sheet-like member with flexibility. The flexibility refers herein to a property that allows the base member 21 to easily bend and conform to the shape of the surface of the fixed member to which the fixing member is applied. The base member 21 may have extensibility and/or stretchability. When the base member 21 is extended or stretched, the deformation may be elastic deformation, or it may elastically deform with a portion of plastic deformation. If the fixing member 20 is applied in an absorbent article or clothing, the flexibility refers to the extent of rigidity that does not cause the wearer to feel stiffness. The extent of flexibility of the base member 21 may be established as desired based on surface shape, structure, composition, application, and the like of the member to be fixed.

The material of the base member 21 can be selected as appropriate while taking into consideration the flexibility and the like. For example, the base member 21 can include a fiber assembly, a plastic film, a elastomer body or a combination thereof. The material of the base member 21 may be the same as that of the outside sheet 11, and in this case, the base member 21 and the outside sheet 11 may be formed as a single piece.

The base member 21 may be a laminate configured by a sheet-like elastomer body and a fiber assembly with stretchability. In this laminate, the elastomer body and the fiber assembly may be joined by an adhesive or by thermal fusion bonding, or may be joined through a physical method such as weaving, sewing or the like.

An example of an elastomer in the elastomer body is a thermoplastic elastomer. The thermoplastic elastomer contains a hard segment and a soft segment, and the hard segment primarily has the function of molecular chain constraint. The thermoplastic elastomer can be classified according to the type of the hard segment thereof. Examples of thermoplastic elastomers include styrene-based thermoplastic elastomers, olefin-based thermoplastic elastomers (TPO), vinyl chloride-based thermoplastic elastomers, urethane-based thermoplastic elastomers, ester-based thermoplastic elastomers, and amide-based thermoplastic elastomers. The elastomer body may be formed from only one type of a thermoplastic elastomer, or may be a mixture of two or more types of thermoplastic elastomers. The elastomer body may further contain various types of additives (tackifier (an agent that adds tackiness), antioxidants, anti-weathering agents, ultraviolet absorbents, colorants, inorganic fillers, oils or the like).

The fiber assembly is a sheet-like fiber base member configured by long fibers, composite fibers, or a combination thereof. Examples of the sheet-like fiber assemblies include a nonwoven fabric, a woven fabric, and a knitted fabrics. There is no particular limitation on the fiber material by which the fiber assembly is configured, and it can be selected as appropriate by a person skilled in the art. The fiber assembly can include a fiber that can be fusion bonded by heat, for good stretchability, flexibility, and feel to the skin. The fiber from which the fiber assembly is formed can include, for example, one or two or more fiber materials selected from the group consisting of a mixed fiber that includes a polypropylene fiber, a polyester fiber, and a polyolefin fiber, a concentric composite fiber having a polyethylene terephthalate core and a polyethylene layer covering the outer circumferential surface thereof, and, a concentric composite fiber having a polypropylene core and a polyethylene layer covering the outer circumferential surface thereof. The method for producing the fiber assembly is also not particularly limited, and various conventionally known production methods can be used such as the spunbond method, the spunlace method, the thermal bond method, the meltblown method, the needle punched method, and the like.

In order to reduce the engagement of the surface $S_1$ of the grip portion 21a with the surface fastener 30 while maintaining the sufficient flexibility of the base member 21 (fixing member 20), the surface of the base member 21 on the surface fastener 30 side may be configured by the fiber assembly. As described later, the engagement between the surface of the fiber assembly and the surface fastener 30 can be easily reduced by a method of fusion bonding fibers together on the surface portion by heat treatment. By disposing meltable particles or the like on the surface of the fiber assembly and melting the particles by heat treatment, the fibers may be fusion bonded together. Furthermore, the whole base member 21 may be the fiber assembly, from the point of view of ensuring the flexibility of the base member 21. In this case, the base member 21 may be a single layer fiber assembly, or it may be a laminate of a plurality of fiber assemblies.

The flexibility of the base member 21 can be expressed by an areal weight thereof, for example. In one aspect, if the areal weight of the fiber assembly of the base member 21 is in the range not less than 5 g/m², not less than 10 g/m², or not less than 20 g/m², and not more than 600 g/m², not more than 400 g/m², or not more than 200 g/m², the base member 21 can be considered to have flexibility. In one aspect, the areal weight of the fiber assembly may be not less than 30 g/m², and not more than 100 g/m².

The thickness of the base member 21 can be selected as appropriate from the point of view of ensuring the flexibility of the base member 21 and so on. For example, the lower limit of the thickness of the base member 21 may be 50 μm, 70 μm, or 100 μm, and the upper limit of the thickness may be 500 μm, 400 μm, or 300 μm.

An opening may also be provided in the base member 21. A shape of the opening is not particularly limited, and may be the same shape as that of a penetration 33 (opening 34) of the surface fastener 30 to be described below, or may be a different shape. A net-shaped base member can also be used. If the shape of the opening is the same shape as that of the penetration 33 (opening 34) of the surface fastener 30, the opening of the base member 21 and the penetration 33 (opening 34) of the surface fastener 30 can also be overlapped on the fixing member 20.

Figure 5:
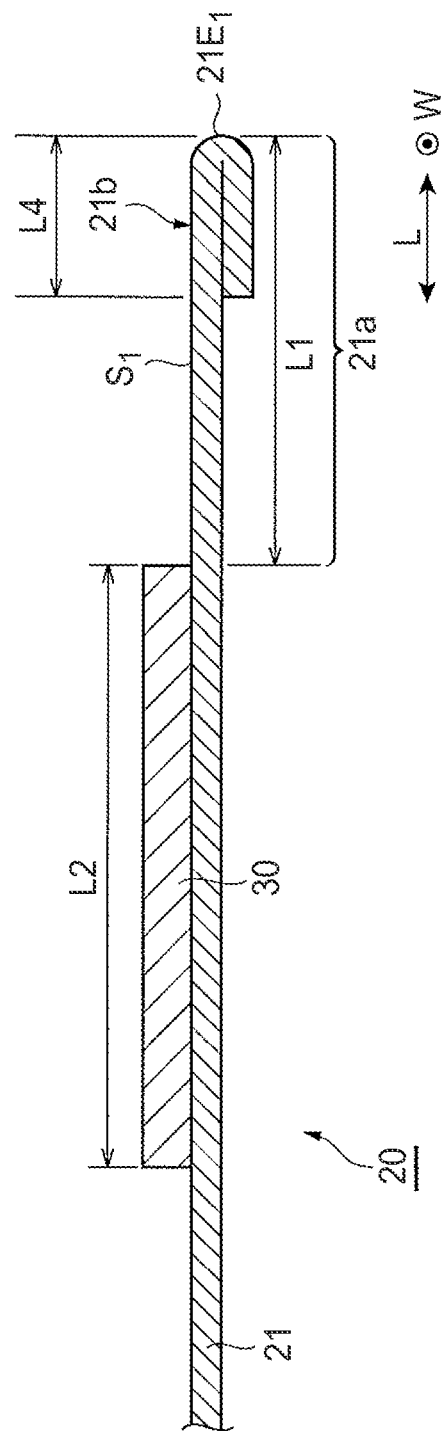
FIG. 5 shows another example of a fixing member.

FIG. 5 is a cross-sectional view showing another example of a fixing member. In the fixing member 20 of FIG. 5, the portion (grip portion 21a) of the base member 21 on the tip end $21E_1$ side of the surface fastener 30 is fixed in a folded back state. According to this aspect, it is possible to give the appropriate stiffness to the grip portion 21a of the base member 21 that has flexibility. The direction of folding back the base member 21 may be opposite to the direction of the surface fastener 30 as shown in FIG. 5, or may be the direction of the surface fastener 30. If the base member 21 is folded back on the surface fastener 30 side, the whole surface $S_1$ including the surface on the surface fastener 30 side in the folded back state may have reduced engagement with the surface fastener 30.

The length L4 of the folded back portion 21b of the base member 21 in the wrap-around direction L may be not more than L1. A lower limit of L4/L1 may be 0.05 or 0.1, and an upper limit thereof may be not more than 1 or 0.9. The lower limit of L4 may be not more than 1 mm or 2 mm, and the upper limit of L4 may be 20 mm or 15 mm.

The folded back portion 21b can be formed by, for example, joining the contacting surfaces together when the base member 21 is folded back by bonding, sewing, welding, or the like. Regardless of the amount of engagement force of the surface $S_1$ of the grip portion 21a with the surface fastener 30, by forming the folded back portion 21b, it is possible to obtain the advantage of improved handlability by providing stiffness.

In one aspect, the lower limit of the ratio of the thickness of the base member 21 to the thickness of the surface fastener 30 (base member thickness/surface fastener thickness) may be 0.12, 0.225 or 0.383. The upper limit of the base member thickness/surface fastener thickness may be 7.6, 5.0, or 3.2.

The lower limit of the thickness of the whole surface fastener 30 may be 60 μm, 90 μm, or 115 μm, and the upper limit of the thickness of the surface fastener (hook member) 30 may be 380 μm, 350 μm, or 320 μm. In the present specification, the surface fastener that satisfies these thickness conditions may be referred to as "low-profile fastener" or "low-profile hook member". The low-profile fastener or low-profile hook member can contribute to reducing the bending stiffness of the portion of the fixing member 20 where the surface fastener 30 is provided, even if grooves or through-holes as described later are not provided.

Figure 6:
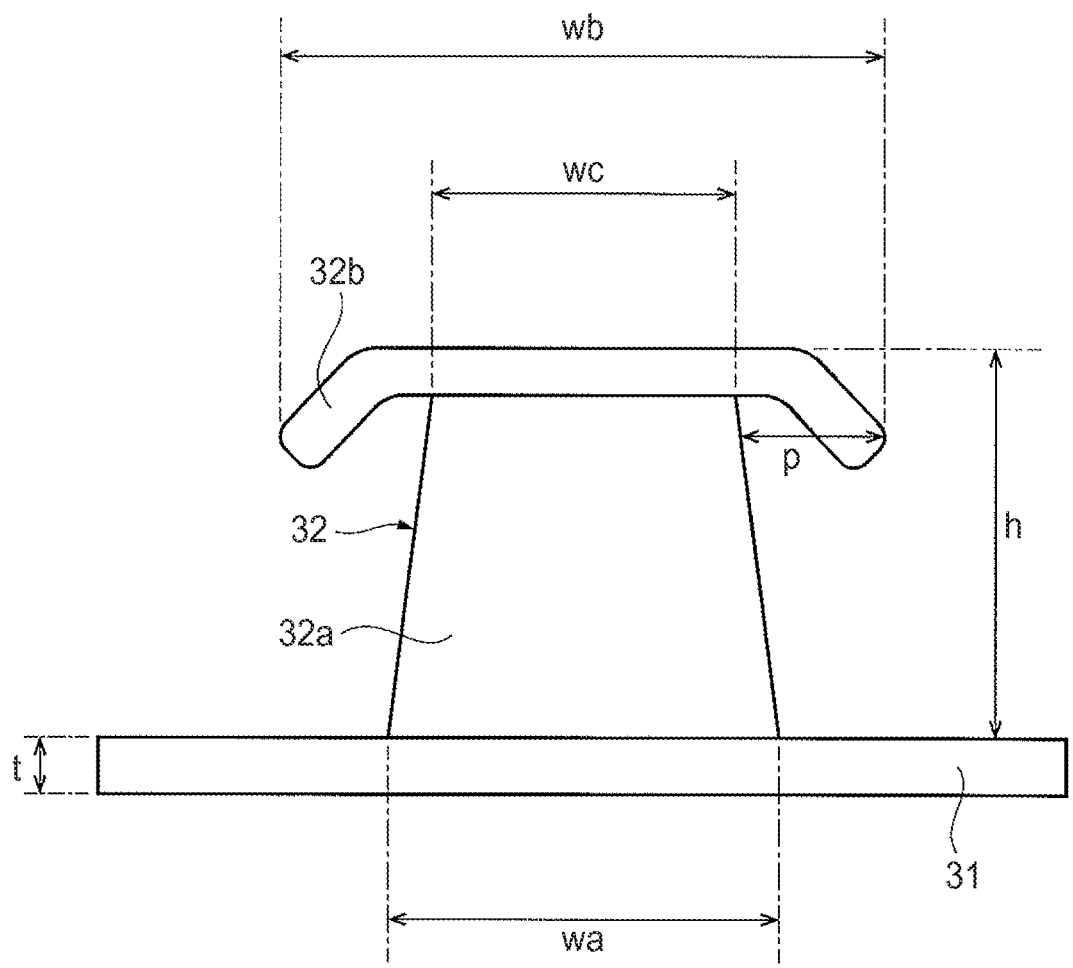
FIG. 6 is a side view showing an example of a hook of a surface fastener (hook member).

FIG. 6 is a side view showing an example of a hook of the surface fastener (hook member) 30. The hook 32 shown in FIG. 6 is provided on a base 31. The hook 32 in several aspects includes a stem portion 32a that extends from the base 31, and an umbrella portion 32b formed on a tip end of the stem portion 32a, and has a mushroom shape as a whole. There is no particular limitation on the shape of the umbrella portion 32b of the hook 32 as long as the umbrella portion 32b is capable of exhibiting the engagement force. Besides the mushroom shape as described above, the shape of the umbrella portion 32b may be a hook shape, a T-shape, or a J-shape.

A lower limit of a thickness of the base of the low-profile hook member may be 20 μm, 30 μm, or 35 μm, and an upper limit of the thickness may be 80 μm, 70 μm, or 60 μm. The lower limit of a height of the hook of the low-profile hook member may be 30 μm, 40 μm, 60 μm, or 80 μm, and an upper limit of the height may be 300 μm, 280 μm, or 260 μm.

There are no particular limitations on a maximum width wa of a bottom of the stem 32a or on a distal width wc of the stem 32a as long as the desired engagement strength can be obtained. Taking the mushroom-shaped hook as shown in FIG. 6 as an example, the lower limit of the maximum width wa for the bottom of the stem portion 32a may be 70 μm or 100 μm, and the upper limit of the maximum width wa thereof may be 250 μm, 200 μm, or 190 μm. In a case of the low-profile hook member, the lower limit of the width wc of the tip end of the stem portion 32a may be 50 μm or 80 μm, and the upper limit of the width wc of the stem portion 32a may be 200 μm, 195 μm, or 185 μm.

The maximum width wb of the umbrella portion 32b of the low-profile hook member may also be determined as appropriate while taking into consideration the engagement force. As shown in FIG. 6, the maximum width wb of the umbrella portion 32b may be larger than the width wa of the bottom. The upper limit of the ratio of the maximum width wb of the umbrella portion 32b to the width wa of the bottom of the stem portion 32a may be 1.01:1, 2:1, or 3:1. The lower limit of the maximum width wb may be 70 μm or 100 μm, and the upper limit of the maximum width wb may be 350 μm or 340 μm. The lower limit of the overhang amount p of the umbrella portion 32b from the tip end of the stem portion 32a may be 5 µm or 10 µm, and the upper limit of the overhang amount p thereof may be 90 µm, 85 µm, 80 µm, or 75 µm.

FIGS. 7 to 21 are views for describing examples of the surface fastener or the shape and arrangement of the surface fastener. The surface fasteners illustrated therein may be low-profile fasteners, but even normal surface fasteners can have the sufficient flexibility.

Figure 7:
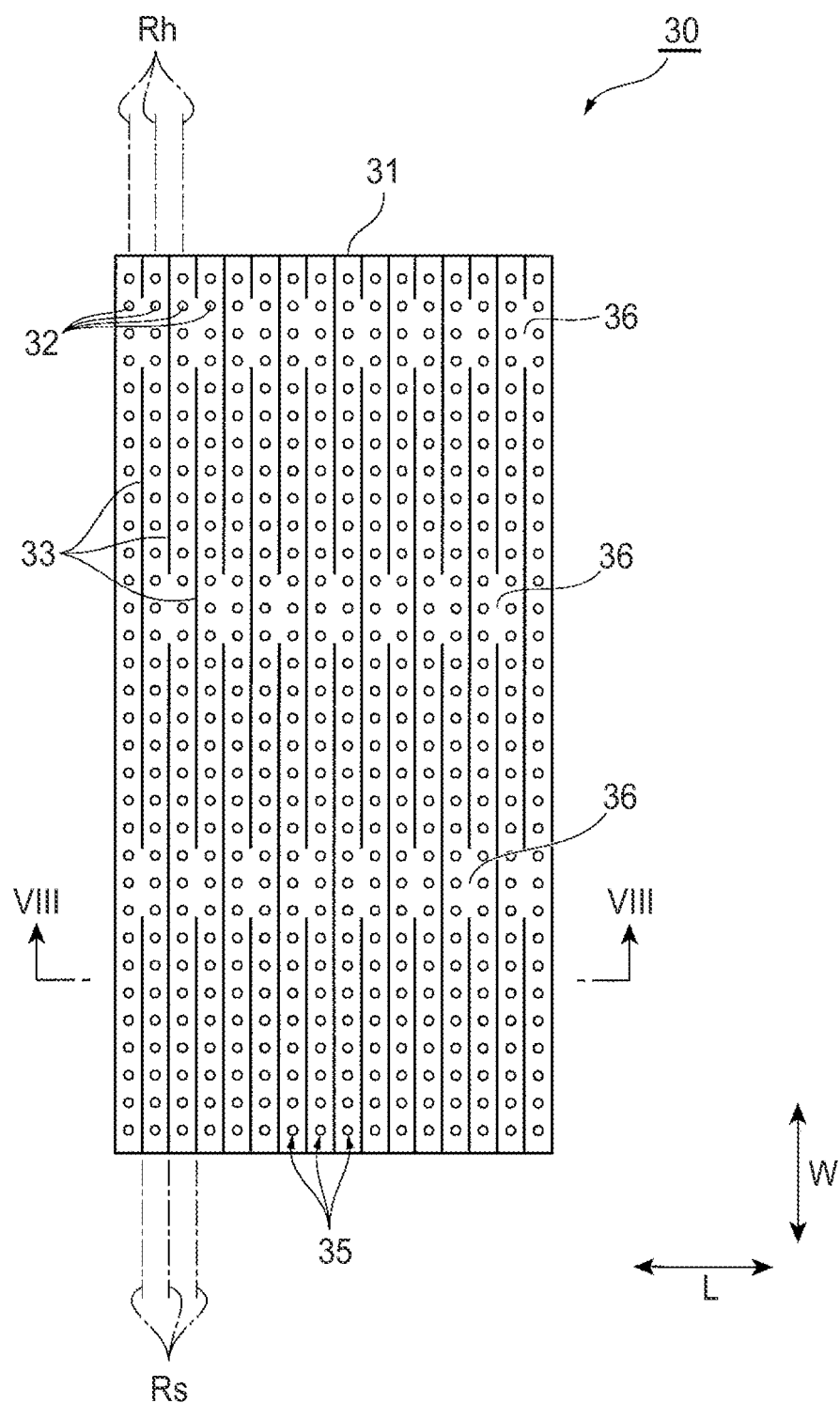
FIG. 7 shows an example of a surface fastener (hook member).

The surface fastener 30 shown in FIG. 7 is the hook member that includes a sheet-like base 31, and a plurality of hooks provided on the base 31. Hook rows Rh are formed by arranging the plurality of hooks 32 along the width direction W. Moreover, a plurality of hook rows Rh is arranged on the base 31 along the direction L with gaps therebetween.

In the surface fastener 30 of FIG. 7, a plurality of slit-like grooves or penetrations 33 is formed between the hook rows Rh that are adjacent to each other in the direction L. By disposing these grooves or penetrations 33 at intervals in the direction W, rows Rs of the grooves or penetrations are formed (hereinafter, sometimes 'rows of slits Rs'). In the present specification, the region 36 between the adjacent grooves or penetrations 33 within a single row of slits Rs is sometimes referred to as a 'linking portion'. In the example of FIG. 6, the linking portions 36 are aligned in a staggered manner.

The surface fastener 30 includes long and narrow regions held between the adjacent rows of slits Rs in the direction L. In the present specification, these long and narrow regions held between the adjacent rows of slits Rs are sometimes referred to as 'strands'.

In the example of FIG. 7, a single row of hooks Rh is configured by a plurality of hooks 32 disposed along a single strand. In other words, the number of hooks 32 in the width direction (direction L) of a strand 35 on which a row of hooks Rh is provided is one. In other words, the strand 35 may have a width corresponding to one hook (the length including the width of the hook and the adjacent portions where the hook 32 is not provided).

Figure 8A:
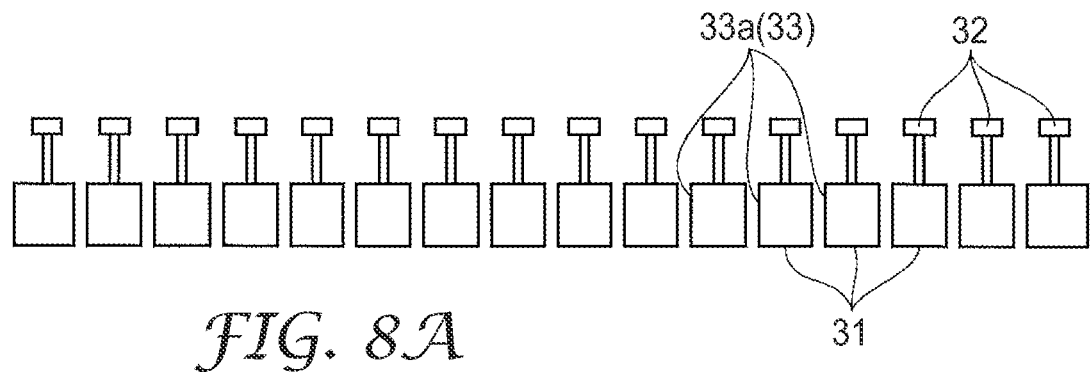
FIGS. 8A, 8B, and 8C are cross-sectional views taken along a line VIII-VIII of FIG. 6.
Figure 8B:
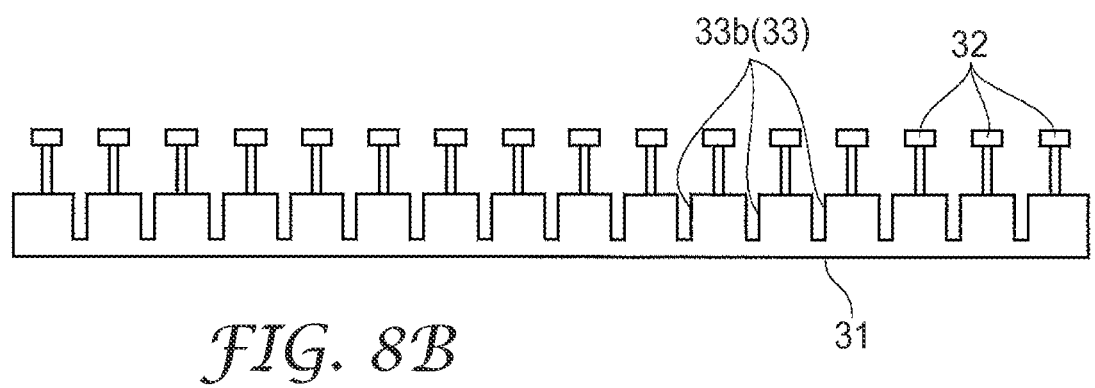
Figure 8C:
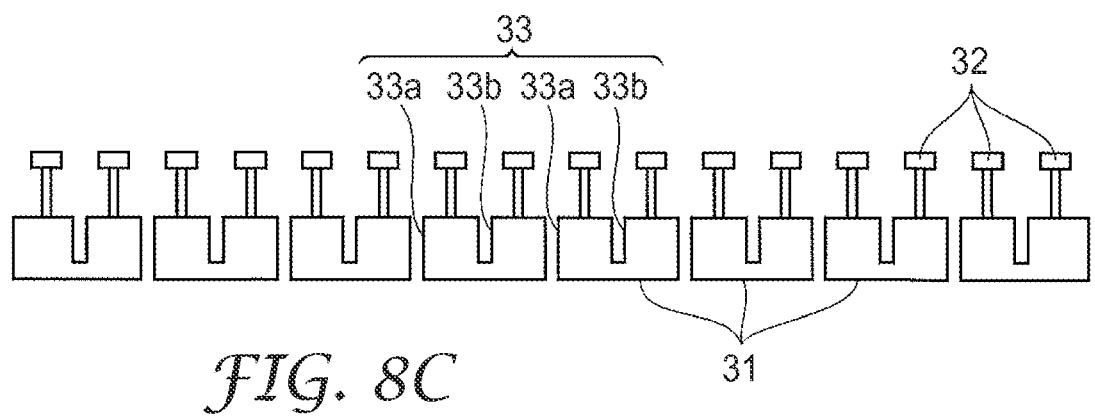

FIGS. 8A, 8B, and 8C are cross-sectional views taken along a line VIII-VIII of FIG. 7. FIG. 8A shows an example in which penetrations 33a are formed, FIG. 8B shows an example in which grooves 33b are formed, and FIG. 8C shows an example in which both penetrations 33a and grooves 33b are formed. In the examples of FIGS. 8B and 8C, the grooves 33b have a constant depth. A lower limit of the ratio of a depth of the grooves 33b to a thickness of the base 31 may be 0.4, and an upper limit of the ratio may be 0.9. In the example of FIG. 8C, the penetrations 33a and the grooves 33b may be disposed alternately.

In the present specification, the term 'penetration' means a hole or an opening provided in the base 31 of the surface fastener 30 that penetrates from the surface of the base 31 on the hook 32 side to the surface of the base 31 on the opposite side to the hooks 32. In the examples in FIG. 7 and FIG. 8, the slit-like penetrations 33a are formed, but penetrations also includes openings 34 as described later. However, the range encompassed by the term 'penetration' is not limited thereto. For example, the 'penetrations' include point-like holes as well as slits that penetrate the base 31 in a straight line, wavy, chevron, or undulating form.

In the present specification, the term 'groove' means a hole or an opening that is formed on the surface of the base 31 on the hook 32 side, and that does not penetrate the surface of the base 31 on the opposite side to the hooks 32. In the examples in FIGS. 7 and 8, the grooves 33b are slit-like grooves, but the range encompassed by the term 'groove' is not limited thereto. For example, 'grooves' include recesses that extend in a two-dimensional (planar) manner, as well as linear recesses.

A length of the slit-like grooves or penetrations may be set as desired. For example, a lower limit of the length of each slit-shaped groove or penetration 33 may be 8 mm, 10 mm, or 12 mm. Alternatively, the slit-shaped grooves or penetrations 33 can be specified by the ratio of the length of the slit-shaped grooves or penetrations 33 in the slit row Rs with respect to the total length of the surface fastener 30 along the row of slits Rs (total length of the slit-shaped grooves or penetrations/length of the row of slits Rs). For example, this ratio may be not less than 40% or not more than 50%.

A length of the linking portion 36 may also be set as desired. For example, a lower limit of the length of the linking portion 36 may be 0.25 mm, 0.5 mm, or 0.75 mm, and an upper limit of the length may be 10 mm, 15 mm, or 20 mm.

The normal hook member may have the configuration as shown in the example in FIG. 6. There is no particular limitation on the shape of the umbrella portion 32b of the hook 32 as long as the umbrella portion 32b can exhibit the engagement force for the normal hook member the same as for the low-profile hook member. Besides the mushroom shape as described above, the shape of the umbrella portion 32b may be a hook shape, a T-shape, or a J-shape.

A thickness and a height of a normal hook member as surface fastener 30 can be set, for example, as described below from the view point of ensuring stability for preventing displacement in the fixing member and the ability to follow the movement of the fixed member.

The lower limit of the thickness t of the base 31 may be 0.025 mm or 0.064 mm, and the upper limit of the thickness t of the base 31 may be 0.512 mm or 0.254 mm.

The lower limit of the height h of the hook 32 may be 0.1 mm or 0.18 mm, and the upper limit of the height h of the hook 32 may be 1.27 mm, 0.51 mm, or 0.33 mm.

There are no particular limitations on a maximum width wa of the bottom of the stem 32a or on the distal width wc of the stem 32a as long as the desired engagement strength can be obtained. For the example of the mushroom-shaped hook as shown in FIG. 6, the lower limit of the maximum width wa of the bottom of the stem 32a and the width wc of the tip end of the stem 32a may be 0.076 mm or 0.127 mm, and the upper limit thereof may be 0.635 mm or 0.450 mm. As shown in FIG. 6, the maximum width wb of the umbrella portion 32b may be larger than the width wa of the bottom of the stem portion 32a, the maximum width wb of the umbrella portion 32b may be the same as the width wa of the bottom of the stem portion 32a. The ratio of the widths wa and wb can be set in the same way as for the low-profile hook member as described above. A lower limit of an overhang amount p of the umbrella portion 32b from the tip end of the stem portion 32a may be 0.013 mm or 0.025 mm, and an upper limit of the overhang amount p may be 0.254 mm or 0.127 mm.

The surface fastener 30 may, for example, be molded from thermoplastic resin. The hook member serving as the surface fastener 30 may be manufactured, for example, as a molded body in which the base 31 and the hook 32 are formed as one piece. In this case, for example, a sheet member is formed having the base 31 and a plurality of pillars arranged on the base 31, by extrusion molding using a molding plate or dies having a plurality of through holes. Next, the tip end portion of each of the pillars is heated, and for example, crushed into a circular plate shape to form each of the hooks 32 having the umbrella portion 32b, thereby obtaining the hook member (surface fastener) 30.

Examples of the thermoplastic resins for forming the surface fastener 30 include polyolefins such as polyethylene and polypropylene, polyamides such as polyethylene terephthalate and nylon, poly(styrene-acrylonitrile), poly (acrylonitrile-butadiene-styrene), plasticized vinyl chloride, polyesters, and the like. Only one type of these thermoplastic resins may be used, or a polymer blend containing a mixture of two or more types of the thermoplastic resin may be used. A polyethylene-polypropylene copolymer may also be used.

In the embodiment as described above, the surface fastener is the hook member, but the surface fastener may be a loop member having a base and loops (engagement portion). In this case, the height of the loop (engagement portion) formed on the base can be established in the same way as the hooks 32 in the above embodiment.

The slit-like grooves and penetrations 33 can be formed using an arbitrary technique. For example, the slit-like grooves 33b and the penetrations 33a can be formed by cutting means such as a blade or a laser device or the like, so that the grooves 33b extend from the surface of the base 31 on the hook 32 side to a constant depth into the base 31, and the penetrations 33a extend from the surface of the base 31 on the hook 32 side to the surface opposite the hook 32 side.

The shape of the surface fastener is appropriately selected from the point of view of ensuring the stability for preventing displacement in the fixing member obtained and the ability to follow the movement of the member to be fixed. The shape of the surface fastener may be, for example, a rectangular shape, a circular shape, an oval shape, an elliptical shape, a polygonal shape, or a combination thereof. A plurality of surface fasteners of the same or different shapes may be provided on the same base member.

Figure 9:
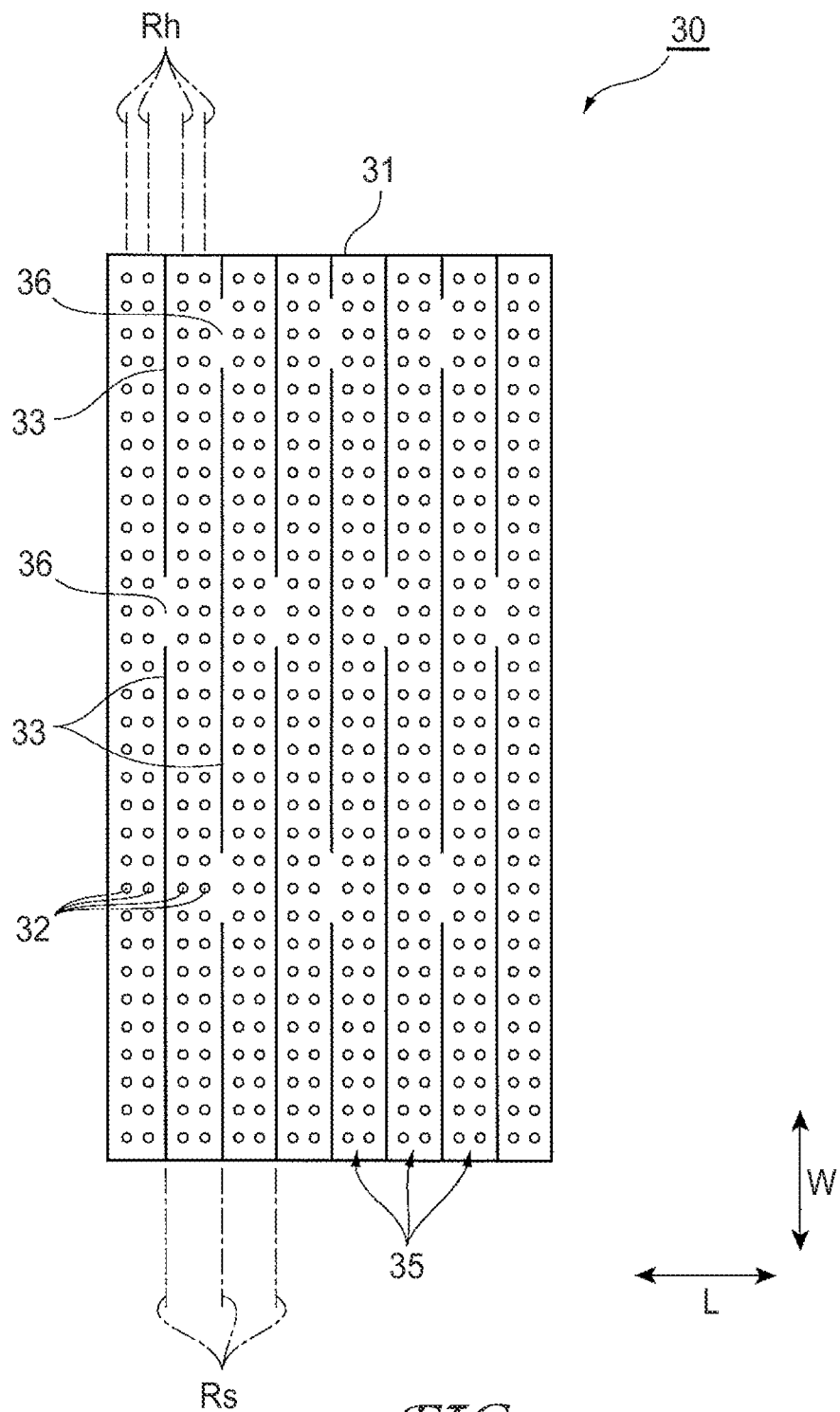
FIG. 9 shows another example of surface fastener (hook member).

The width of the strand 35 is not limited. For example, as shown in FIG. 9, the width of the strand 35 may also be a width corresponding to two hooks. The width of the strand 35 may correspond to three or more hooks 32. The maximum width of the strand 35 may also correspond to ten hooks 32.

There is no limitation regarding the spacing of rows of slits Rs. For example, the lower limit of the number of rows of slits Rs per cm in the direction orthogonal to the rows of slits Rs may be one, and the upper limit of the number thereof may be ten.

Figure 10:
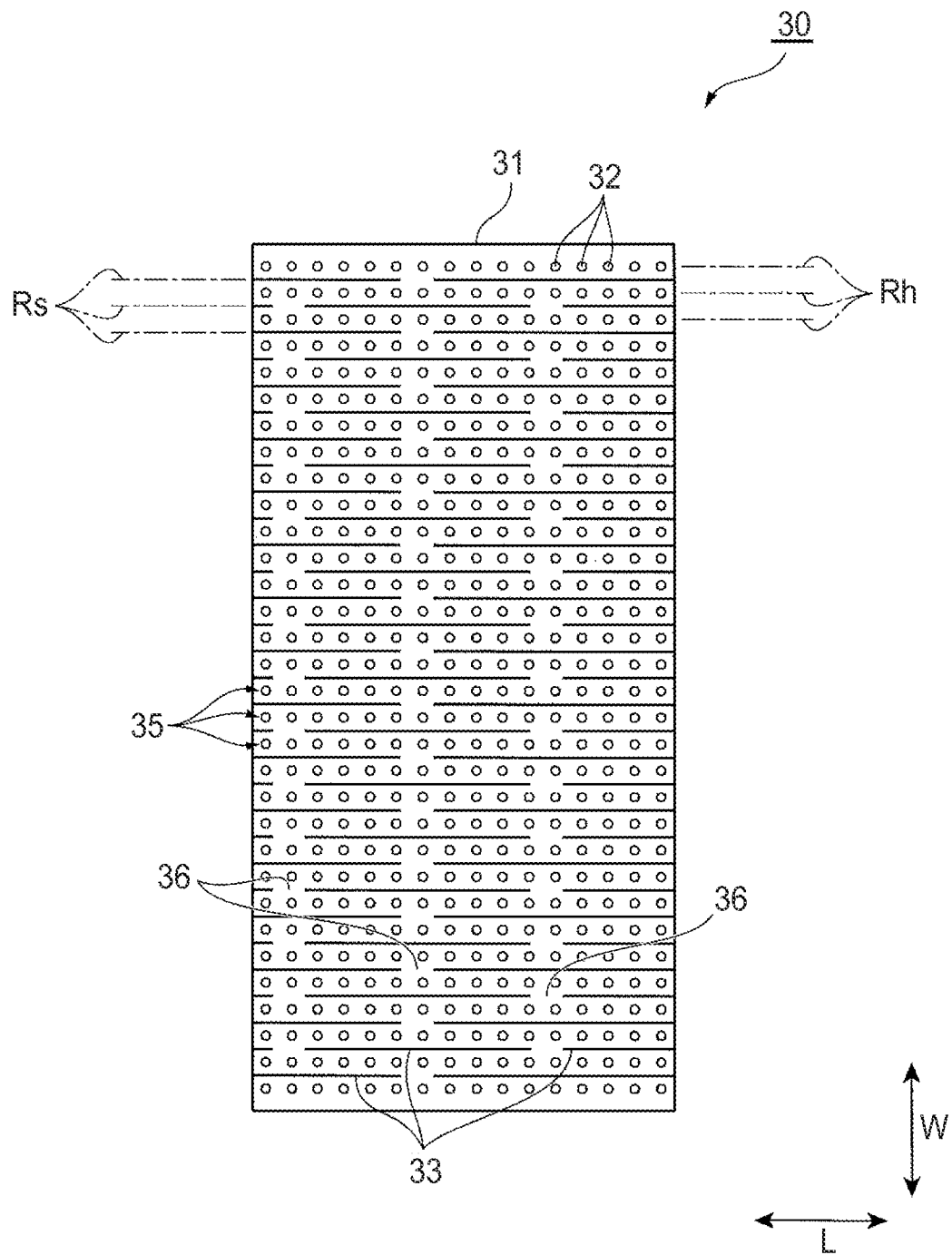
FIG. 10 shows another example of surface fastener (hook member).

The direction in which the slit-like grooves or penetrations 33 extend is also not limited. For example, as shown in FIG. 10, each row of slits Rs may be formed along the direction L. Alternatively, each of the rows of slits Rs may also be slanted at any desired angle θ (0°<θ<90°) with respect to the wrap-around direction L or the width direction W.

Figure 11:
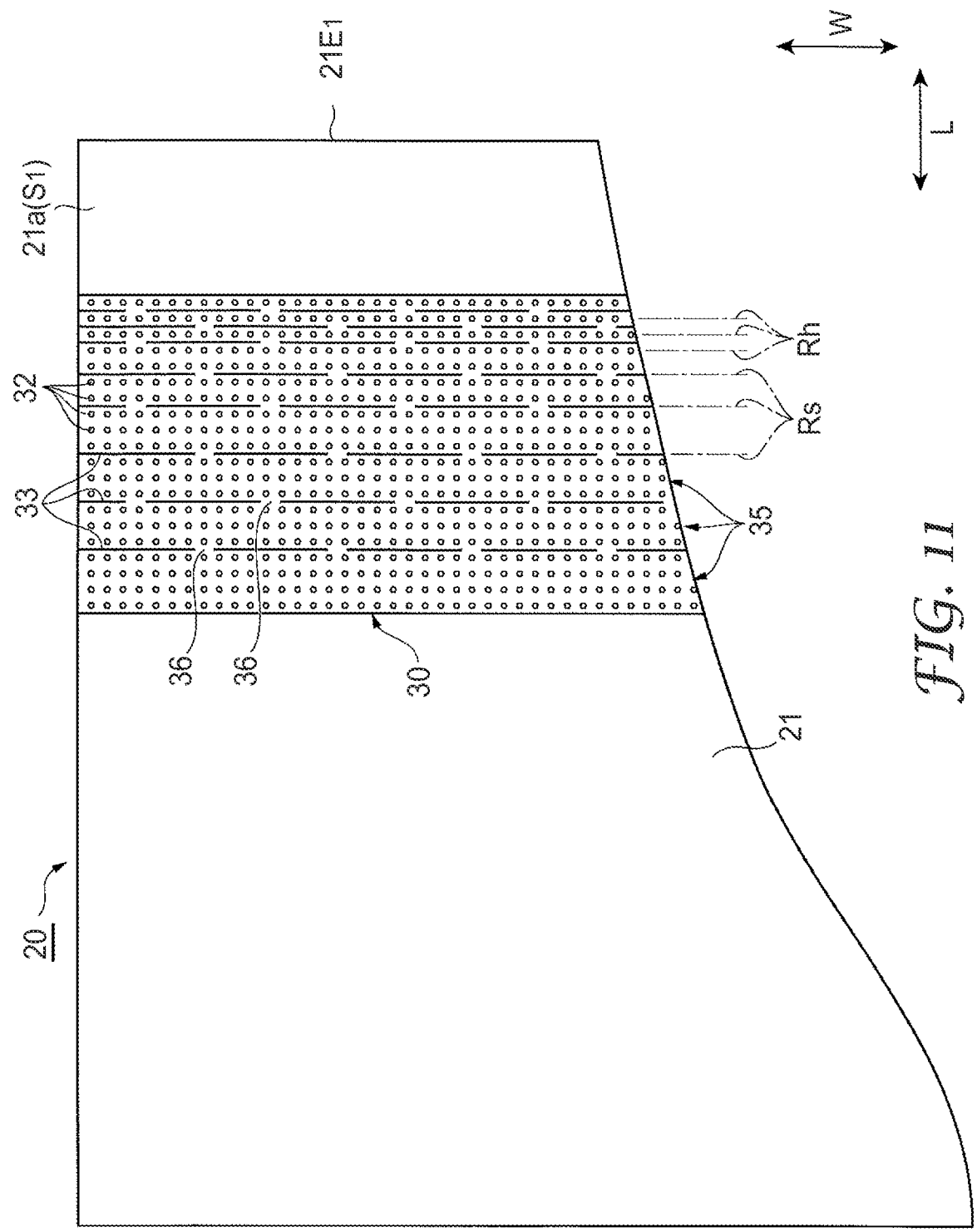
FIG. 11 shows another example of fixing member.
Figure 12:
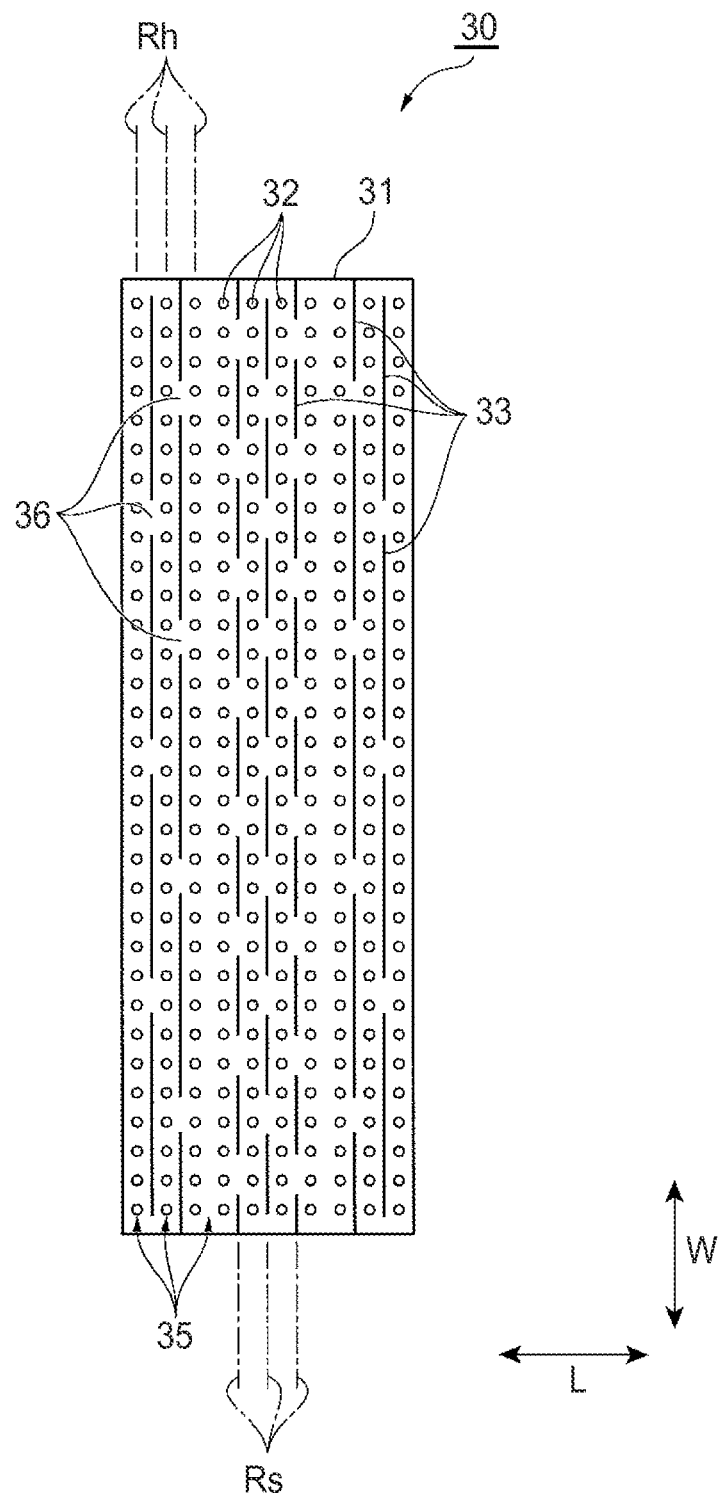
FIG. 12 shows another example of surface fastener (hook member).

The width of the strands 35 may be non-uniform. For example, as shown in FIG. 11, the slits 33 may be formed so that the width of the strands 35 becomes gradually narrower towards the tip end 21E$_1$ of the base member 21. Alternatively, as shown in FIG. 12, a mixture of strands 35 containing only a single hook row Rh and strands 35 containing two hook rows Rh may be used.

Figure 13:
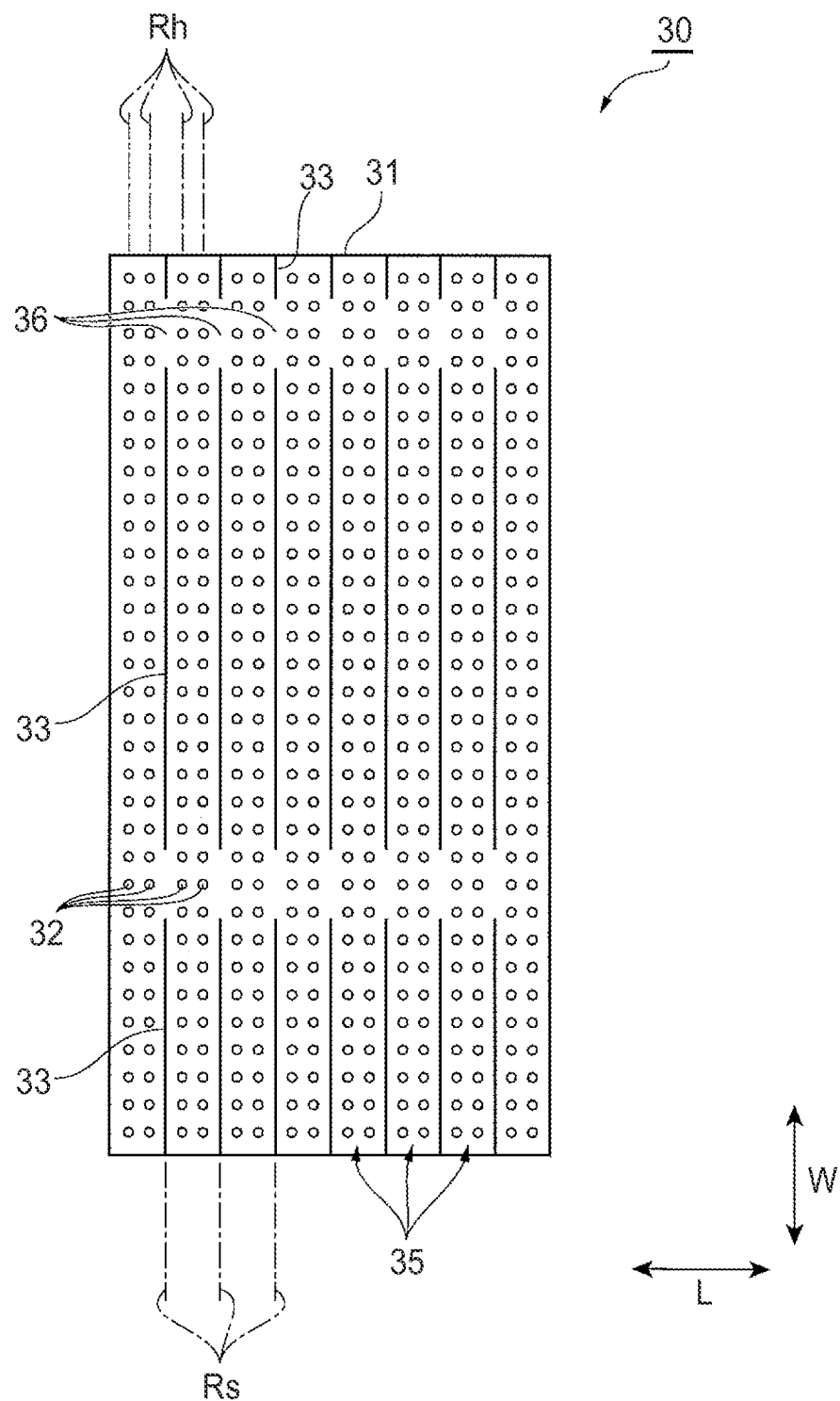
FIG. 13 shows another example of surface fastener (hook member).

The configuration of the linking portions 36 is not limited to a staggered arrangement as shown in FIG. 7. For example, as shown in FIG. 13, any desired adjacent linking portions 36 may be arranged side by side along a direction orthogonal to the slit row Rs (the wrap-around direction L in FIG. 13).

Figure 14:
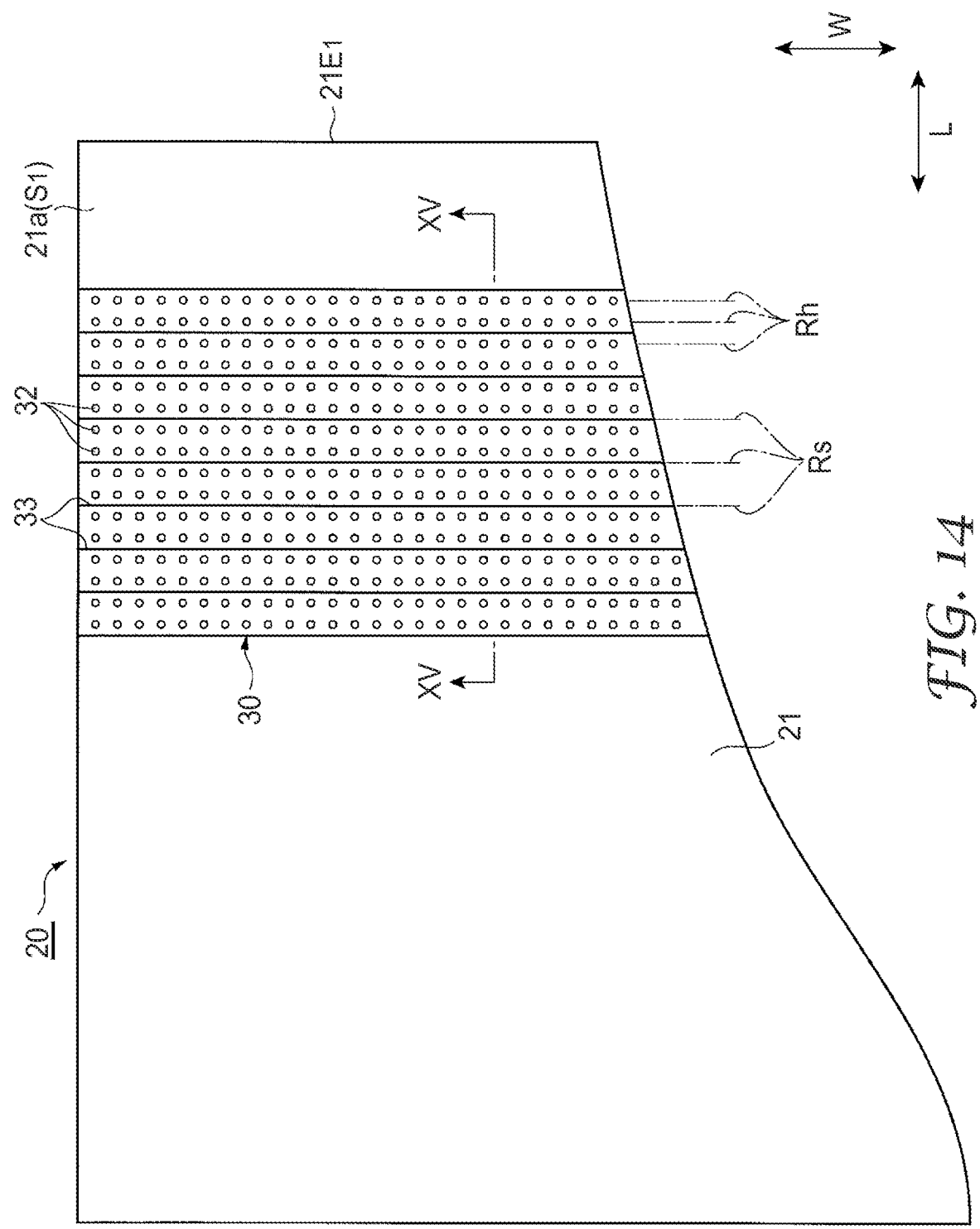
FIG. 14 shows another example of fixing member.

As shown in FIG. 14, a single slit-like groove or penetration 33 may extend without interruption from one side of the surface fastener 30 to the opposite side. In this case, there is no linking portion 36 on the surface fastener 30.

Figure 15A:
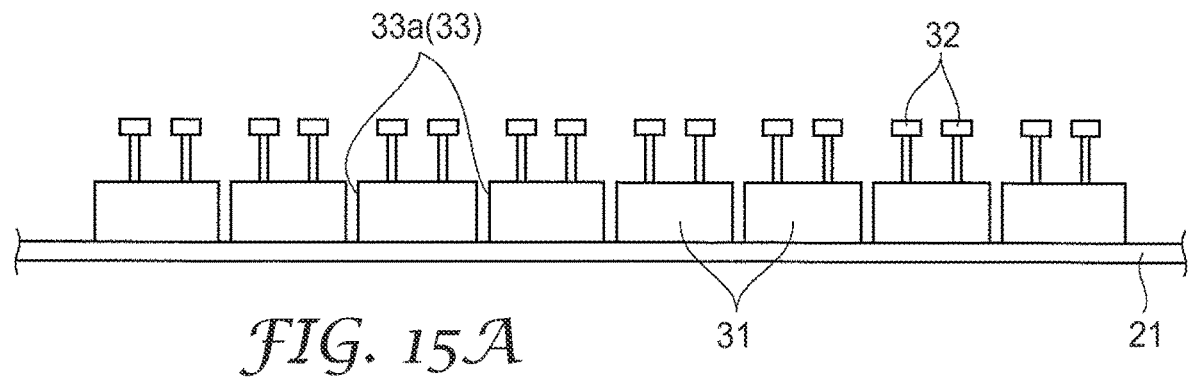
FIGS. 15A, 15B, and 15C are cross-sectional views taken along a line XV-XV of FIG. 14.
Figure 15B:
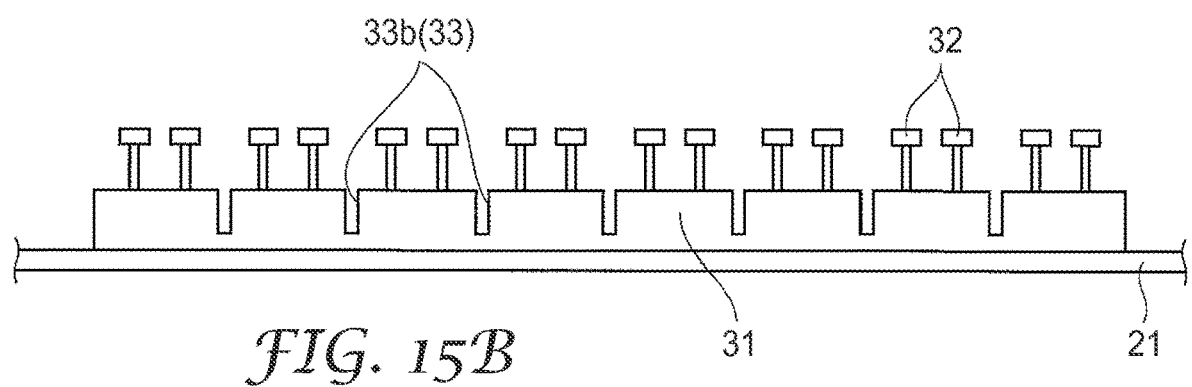
Figure 15C:
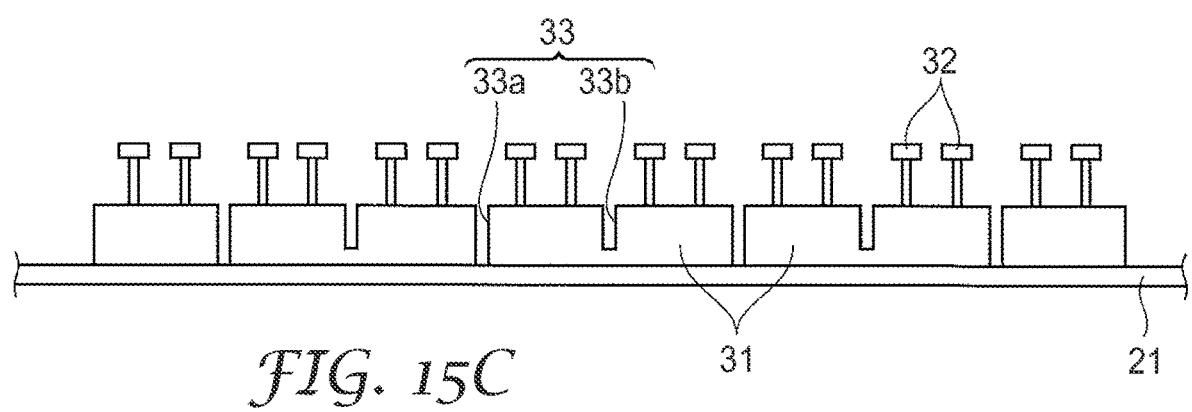

FIGS. 15A, 15B, and 15C are cross-sectional views taken along a line XV-XV of FIG. 14. As shown in FIG. 15A, all slits may penetrate the base 31, and slit-like penetrations are formed. As shown in FIG. 15B, all the slits may be grooves, and the grooves 33b have a uniform depth from the surface of the base 31 on the hook 32 side. In addition, as shown in FIG. 15C, penetrations 33a and grooves 33b may be disposed alternately. In a case in which the slit 33 is a groove, the lower limit of the ratio of the depth of the slit 33 to the thickness of the base 31 may be 0.4, and the upper limit thereof may be 0.9.

In the surface fasteners 30 shown in FIGS. 16 to 20, a plurality of openings 34 is formed as penetrations in the base 31.

Figure 16:
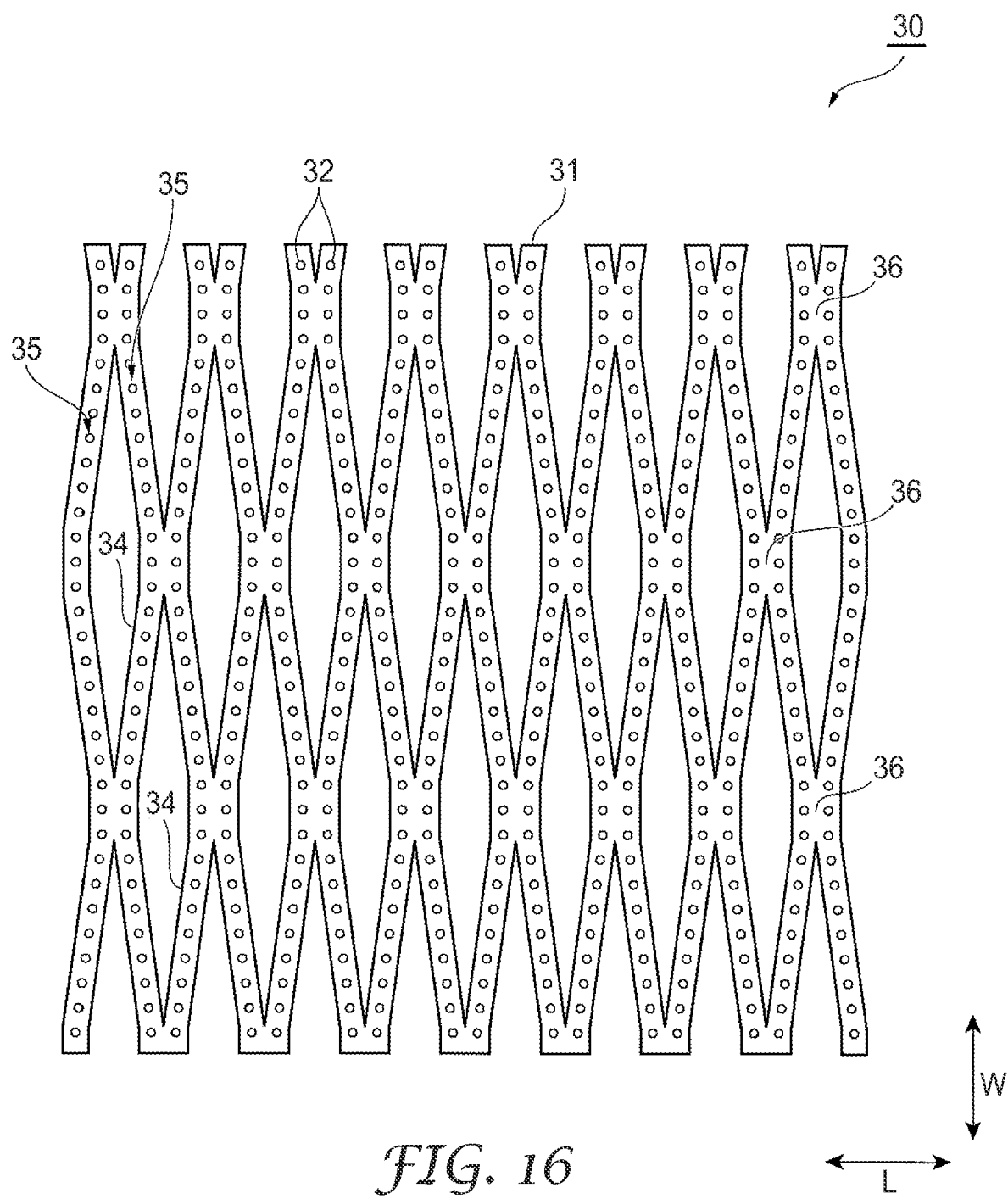
FIG. 16 shows another example of surface fastener (hook member).

The openings 34 in the surface fastener 30 shown in FIG. 16 are slit-like openings that extend along the direction W, and are formed by expanding in the wrap-around direction L. In this example, the width of each strand 35 corresponds to one hook 32, and the openings 34 and linking portions 36 are aligned in a staggered manner respectively.

The openings 34 in the surface fastener 30 shown in FIG. 16 are roughly diamond shaped, but the shape of the openings is not limited thereto. For example, the openings may also be hexagonal, and if openings of this type are aligned in a staggered manner, the surface fastener 30 has a honeycomb structure. Alternatively, the openings may be circular, elliptical, rectangular, star shaped, waveform shaped, or another polygonal shape.

Figure 17:
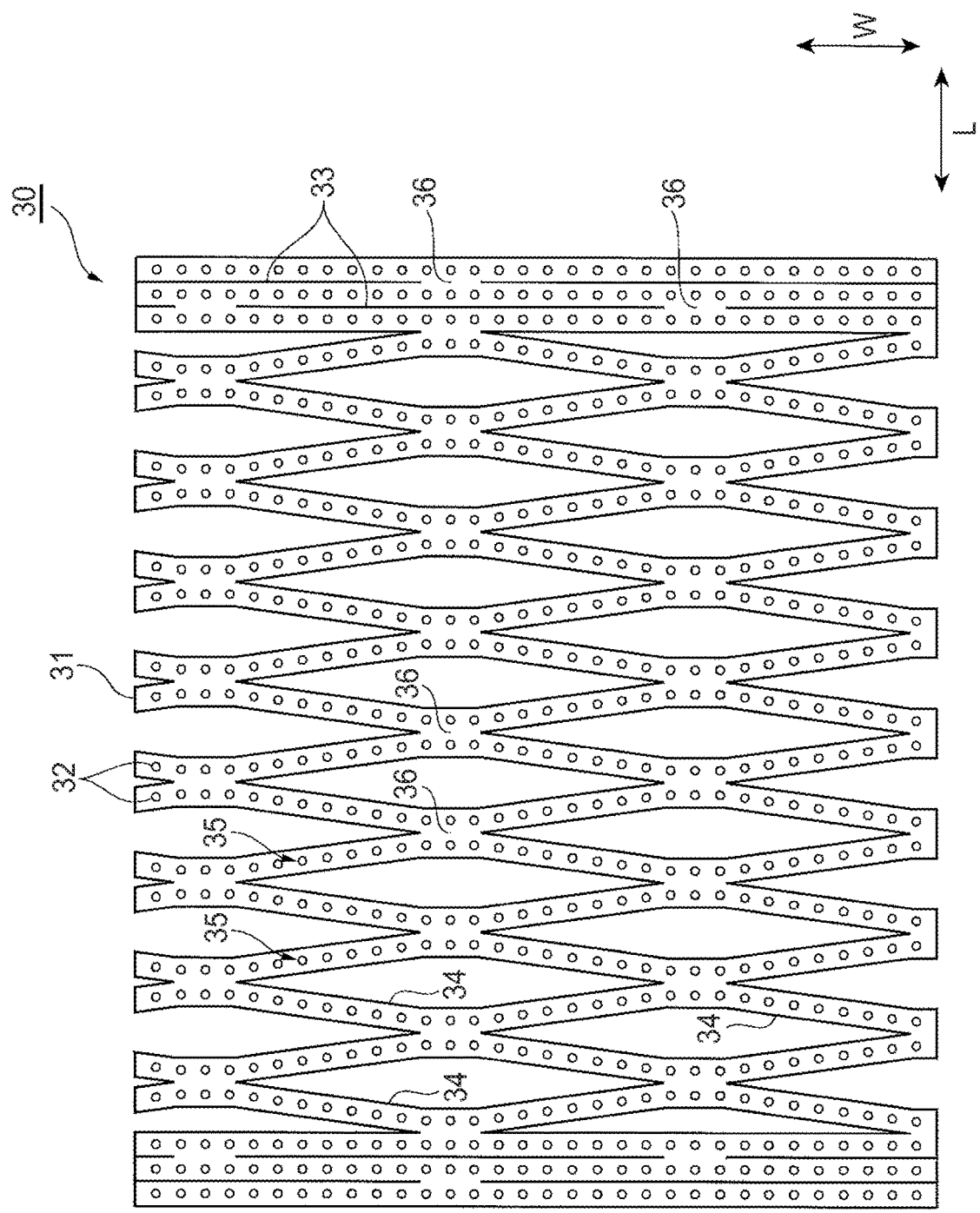
FIG. 17 shows another example of surface fastener (hook member).

As shown in FIG. 17, both openings 34 and slit-like grooves or penetrations 33 may be formed by expanding only a portion of the plurality of slits. In this example, the openings 34 are provided in the center portion of the surface fastener 30, and the slit-like grooves or penetrations 33 are provided near both ends of the surface fastener 30. However, the positions of the slit-like grooves or penetrations 33 and openings 34 are not limited thereto. For example, the slit-like grooves or penetrations 33 may be provided in the center portion, and the openings 34 may be provided near both ends.

Figure 18:
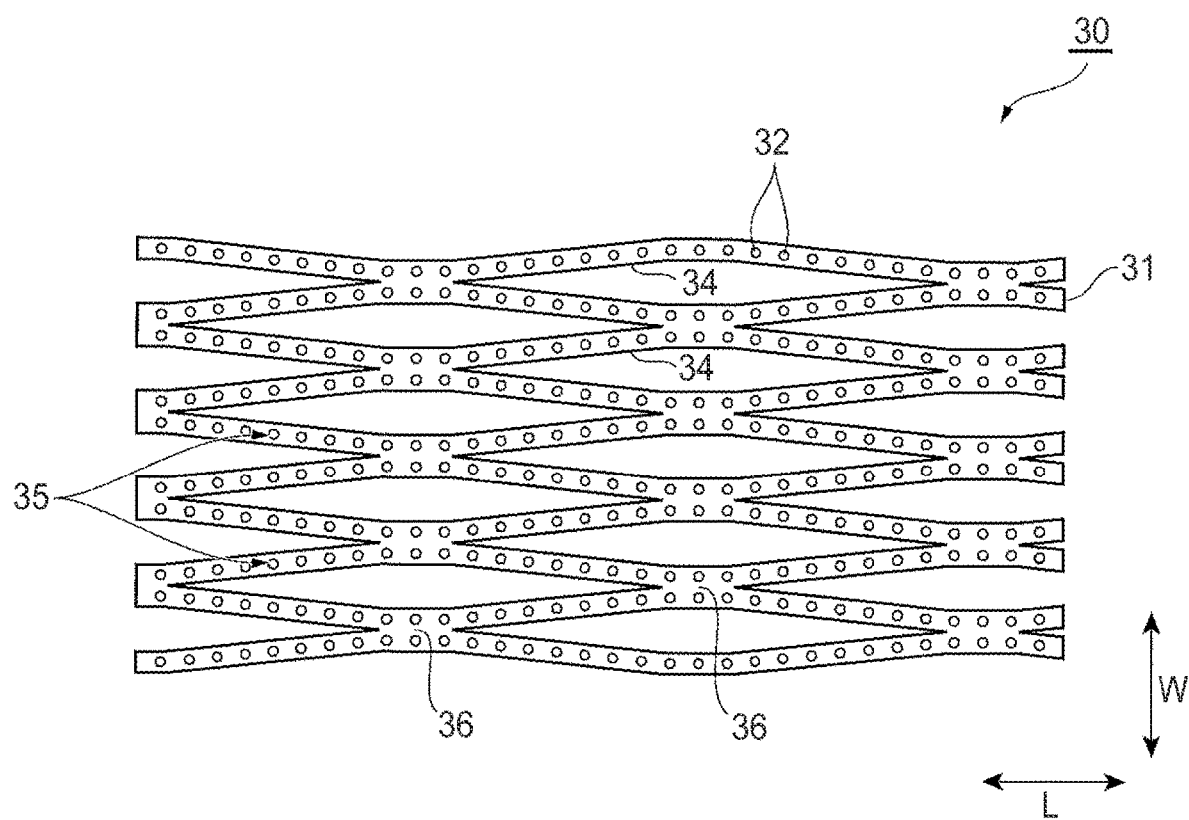
FIG. 18 shows another example of surface fastener (hook member).

The openings 34 in the surface fastener 30 shown in FIG. 18 are formed by widening slits that extend in the wrap-around direction L. In this way, the extension direction of the slit-shaped penetrations 33, which become the basis for the openings, is not limited.

If the surface fastener 30 has openings, there is no limitation to the width of the strands 35. For example, the width of each strand 35 may be equivalent to a portion containing two hooks 32, and the maximum value of the width thereof may be equivalent to a portion containing ten hooks 32. The width of the strands 35 may also be non-uniform, for example, as shown in FIG. 19, the openings 34 may be formed such that the width of the strands 35 gradually narrows towards the tip end of the base member 21.

Figure 19:
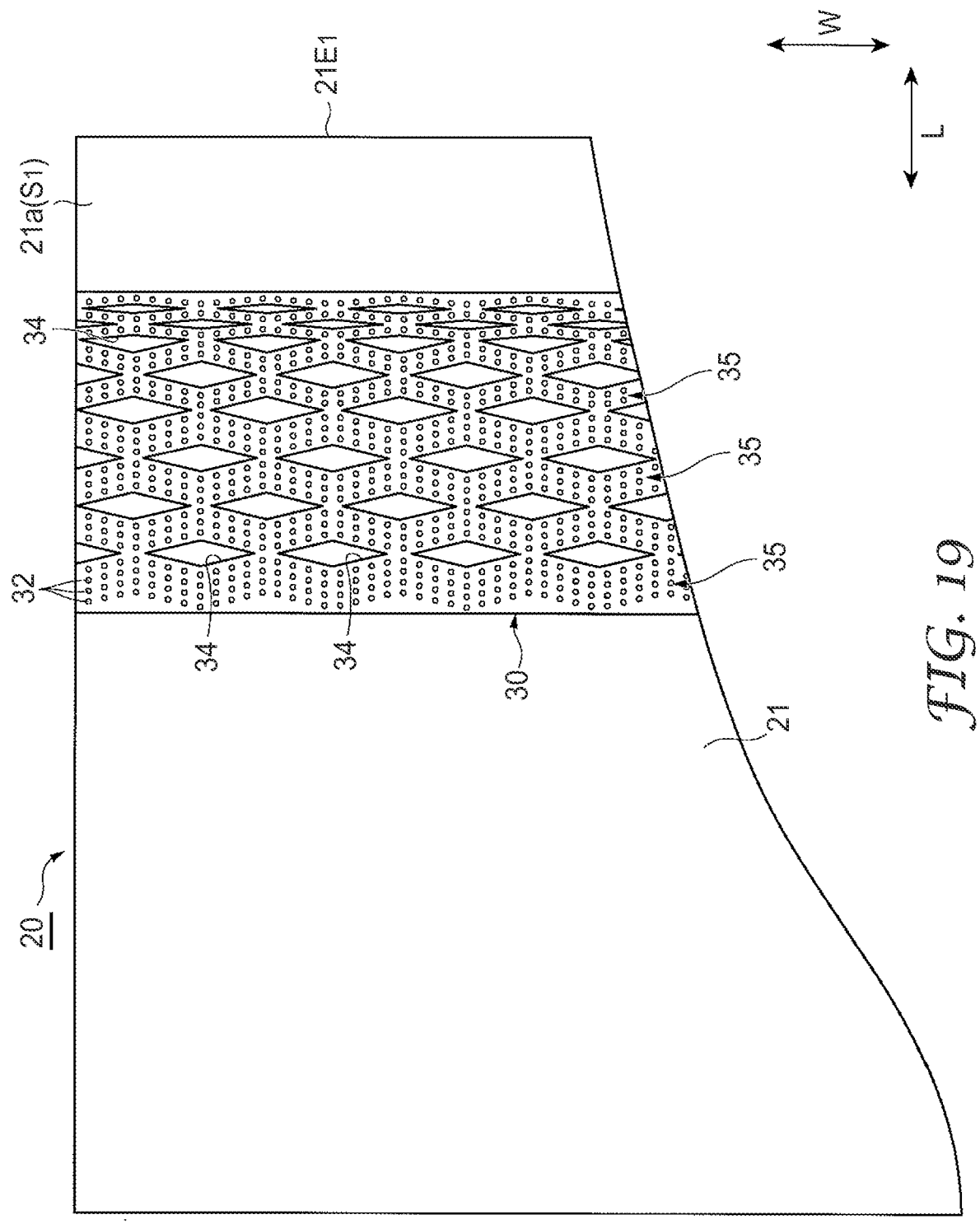
FIG. 19 shows another example of a fixing member.
Figure 20:
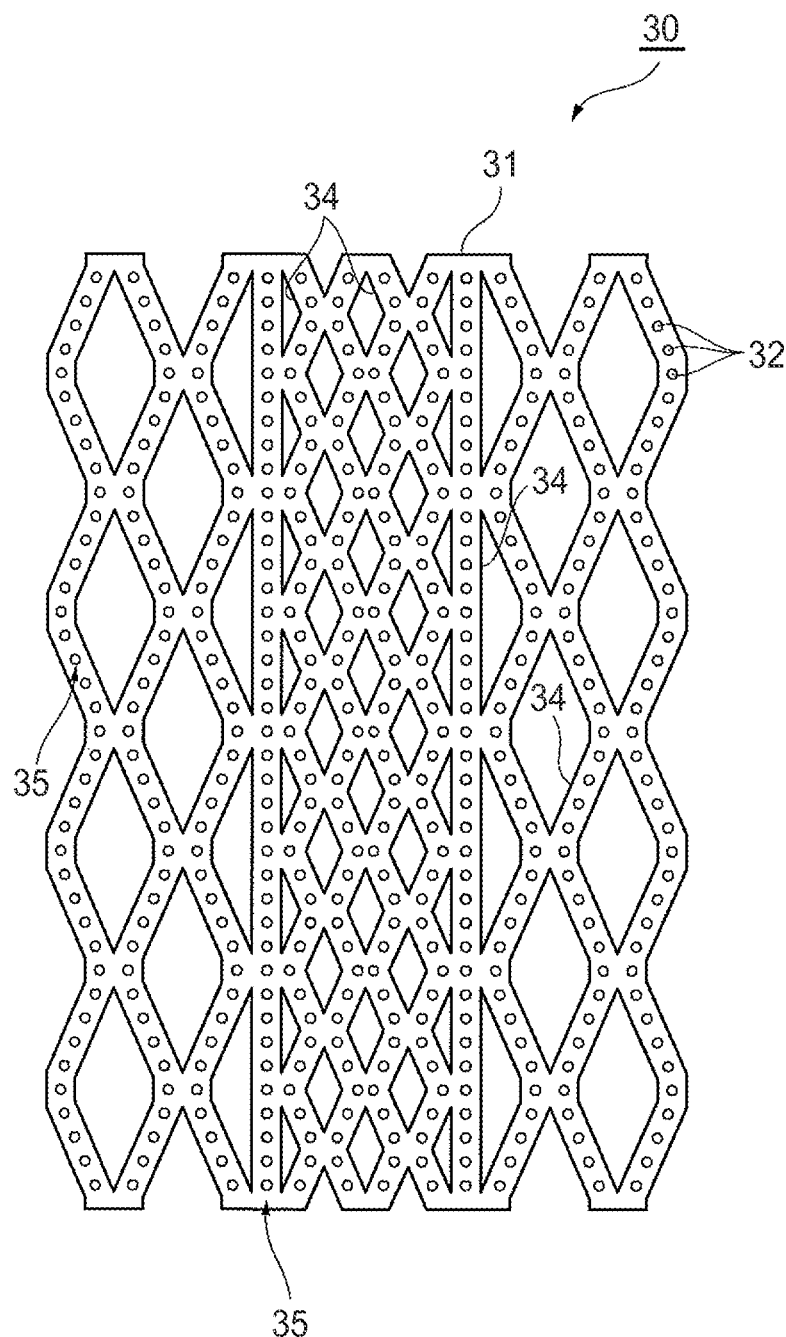
FIG. 20 shows another example of surface fastener (hook member).

The size of the openings 34 is not required to be uniform, for example, as shown in FIG. 19, the size of the openings 34 may be non-uniform. Openings with various types of shapes may be mixed, as shown in FIG. 20.

By forming the grooves or penetrations 33 or the openings 34 in the low-profile surface fastener, the stiffness thereof can be further reduced. In so doing, a further excellent effect can be obtained by reducing the stiffness of the fixing member and the irritation to the skin of the user. However, a sufficient effect can be obtained by forming grooves or penetrations 33, even without the low-profile surface fastener.

Figure 21:
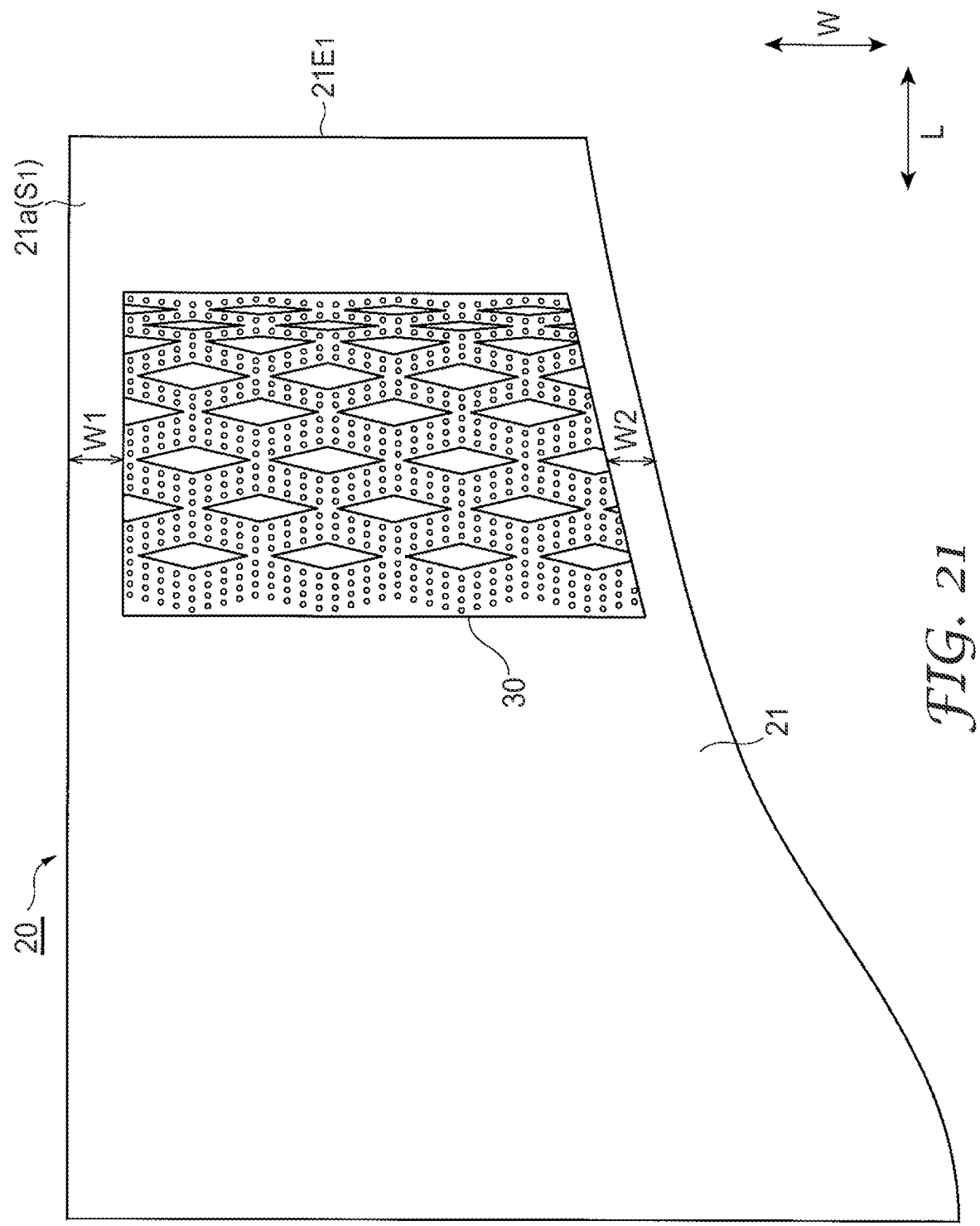
FIG. 21 shows another example of a fixing member.

As shown in FIG. 21, the surface fastener 20 may be disposed in a position distant from the ends in the width direction W of the base member 21. The distance W1 between one edge of the base member 21 and the surface fastener 30 may be in the range from 0 to 4 cm. In one aspect, W1 may be 0 mm, 2 mm, 5 mm, 1 cm, 2 cm, or 4 cm. The distance from the other edge of the base member 21 and the surface fastener 30 can be set in the same way as for W1. This type of arrangement is not limited to the surface fastener 30 in which the openings 34 are formed as shown in FIG. 21.

The openings 34 can be formed, for example, with the hook material on which the slit-like penetrations 33a are formed expanded in the direction orthogonal to the rows of slits. Furthermore, the openings 34 may be formed by hollowing out the hook member to the desired shape, without expanding the hook member. Note that after the slit-like penetrations 33a are formed and affixed to the base member 21, the openings 34 may also be formed by expanding the slit-like penetrations 33a together with the base member 21. Furthermore, after the hook member 30 is affixed to the base member 21, the openings 34 may also be formed by forming slit-like penetrations that penetrate the base member 21 and the hook member 30, and then expanding the hook member 30 together with the base member 21. In this case, the fixing member 20 in which the voids of the substrate 21 and the penetrations 33 (openings 34) of the surface fastener 30 are in an overlapped state is obtained.

Means for stretching the surface fastener to form the openings 34 include machines such as a tenter and a roller, or a manual operation. There is no limitation to the stretch rate of the surface fastener when the openings are formed, the upper limit may be, for example, 50%, 100%, 150%, 200%, 300%, 400%, or 600%. Here, the stretch rate indicates the length of the stretched surface fastener as a percentage of the length (initial length) of the surface fastener 30 in the direction it is stretched. For example, when the length of the surface fastener 30 after stretching is 1.5 times the initial length, the stretch rate is 50%.

The orientation and length of the slit-like grooves or penetrations 33, the orientation, shape, and size of the openings 34, and the position of the linking portions 36 are set such that the surface fastener 30 itself of the fixing member 20 can flexibly change shapes. Accordingly, the benefits such as the flexibility of the overall fixing member, the follow-up properties of the fixing member with respect to the member to be fixed, the reduction of skin irritation in cases in which the fixing member is used in the absorbent article or clothing, and the like are similarly maintained in these various examples of shape changes.

When the surface fastener 30 in which the openings 34 are formed is affixed to the base member 21 via an adhesive or pressure sensitive adhesive, the adhesive or pressure sensitive adhesive thereof may be exposed to the openings 34.

The density of the hooks 32 in the hook member (surface fastener 30) is determined from the total number of hooks in the hook member/total surface area of the base 31 and openings 34 in the hook member. If a plurality of hook members 30 is installed on the base member 21 with gaps therebetween, the surface area of the gaps present between the plurality of hook members 30 is not included in the total surface area. The upper limit of the density thereof, may be, for example, approximately 31 hooks/cm$^2$, or approximately 39 hooks/cm$^2$. Furthermore, the upper limit of the density thereof may be, for example, approximately 1550 hooks/cm$^2$ or 1240 hooks/cm$^2$.

If openings 34 are formed by expanding the hook member 30 in which the slit-like penetrations 33 are formed, and if the hook member 30 is attached to the base member 21 while maintaining the shape of the openings 34 formed thereby, the initial density of the hooks 32 in the hook member 30 before expansion may be set as described below. Namely, the lower limit of the initial density may be, for example, 155 hooks/cm$^2$, 186 hooks/cm$^2$, or 248 hooks/cm$^2$, and the upper limit of the initial density may be, for example, 1,550 hooks/cm$^2$. The initial density of the hooks 32 is determined from the total number of hooks in the hook member/total surface area of the base 31 in the hook material before expansion. If a plurality of hook members 30 is installed with gap therebetween on the base member 21, the range of the initial density described above can be adopted for each of the hook members 30.

The lower limit of the surface area of the surface of the umbrella portions 32b as a percentage of the overall surface area of the hook member 30 when the hook member 30 is attached to the base member 21 (relative density of the umbrella part) may be, for example, 5% or 10%. The upper limit of the percentage may be 24%, 30%, or 40%. If a plurality of hook members 30 is installed on the base member 21, the range for the percentage described above can be adopted for each of the hook members 30 thereof.

From the view point of ensuring the stability for preventing displacement in the fixing member obtained and the ability to follow the movement of a member to be fixed, the range of installation of the surface fastener 30 with respect to the base member 21 can be set based on the length in the width direction W of the fixing member 20 and/or the ratio of the total surface area of the surface fastener 30 relative to the surface area of the base member 21.

The ratio of the total area of the surface fastener 30 to the area of the base member 21 (total area of the surface fastener 30/area of the base member 21) may be not less than 1%, not less than 3%, or not less than 8%, and may be not more than 100%, not more than 90%, or not more than 80%. When the fixing member 20 is fitted to another member as in FIG. 1 (in a case of FIG. 1, the back end part 10b of the main body part 10), the ratio of the total area can be set as the ratio of the area of the surface fastener 30 to the remainder of the area after deducting the area that overlaps with the other member. The total area of the surface fastener 30 means the area of the base 31 plus the area of the openings 34 in cases where openings 34 are formed in the base 31 of the surface fastener 30. In cases in which a plurality of surface fasteners 30 are installed with spaces therebetween, the areas of the spaces is not included. The surface fastener 30 may also be installed on the entire surface of the base member 21. In one aspect, the ratio of the total area of the surface fastener 30 to the area of the base member 21 may be not less than 10% and not more than 70%.

If the installation range of the surface fastener 30 is specified based on the above ratio after the length (width) in the width direction W of the base member 21 is set to nearly the same as or greater than the length in the wrap-around direction L thereof, the width of the surface fastener 30 will become larger. As a result, the fixing member can be provided that can more reliably follow the movement of the member to be fixed without losing the stability for preventing displacement generated between the fixing member and the member to be fixed. In addition, it becomes difficult to bend the base member 21 along the direction W. A plurality of surface fasteners 30 may also be installed on the base member 21 with spacing therebetween.

In this way, even if the installation region of the surface fastener 30 is adequately provided, the flexibility of the base member 21 is not hindered more than necessary. Accordingly, even if a region for the surface fastener 30 is widely fastened in order to ensure the stability for preventing displacement generated between the fixing member and the fixed member, the fixing member follows the movement and the like of the fixed member, and the surface fastener 30 does not easily peel off from the fixed member. Moreover, in applications that use a fixing member with an absorbent article, clothing, or the like, skin irritation of the wearer can be suppressed, and therefore, even if the surface fastener 30 is affixed as far as both ends of the substrate 21 (both ends in the W direction of the substrate 21), there is no concern of the fixing member causing the wearer to feel pain, discomfort, or the like. By using the low-profile surface fastener in this way, even if the region of the surface fastener 30 in the fixing member 20 thereof is expanded, good user-friendliness of the diaper or the other absorbent articles or clothing can be maintained.

The following is a description of one aspect of a method of manufacturing the fixing member having the base member and the surface fastener. The fixing member can be obtained by, for example, a method that includes a step of heat treating a portion of the base member or a raw material base material that includes a portion corresponding to the base member so that the engagement with the surface fastener is reduced. In this case, the engagement between the fiber assembly and the surface fastener can be easily reduced on the heat-treated surface. In several aspects, the base member can be manufactured using a long raw material base material that will form a plurality of base members. The method in these aspects includes, for example, a step of preparing a long raw material base material that will form a plurality of base members; a step of fitting the surface fastener to a region separated from the position corresponding to the tip end of the base member on the raw material base material; a step of heat treating the region between the region where the surface fastener is fitted and the position corresponding to the tip end of the base member so that the engagement with the surface fastener is reduced; and a step of dividing the raw material base material and the laminate having the surface fastener provided on the raw material base material into the plurality of fixing members. The sequence of the steps can be changed as appropriate. For example, either of the step of fitting the surface fastener to the raw material base material and the step of heat treating the surface of the raw material base material may be carried out first, or they may be carried out simultaneously.

Figure 22:
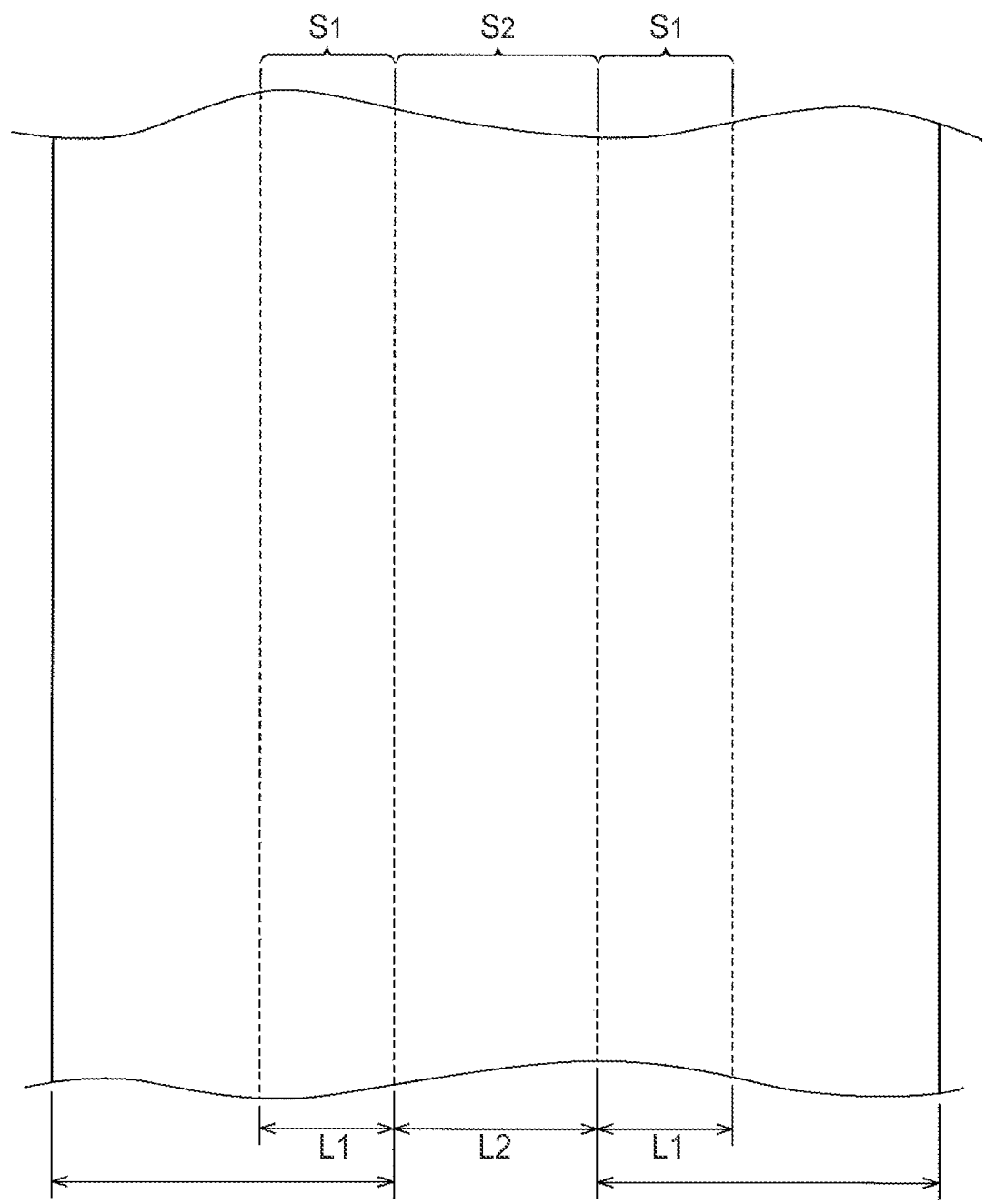
FIG. 22 shows an example of a method of manufacture of the fixing member.
Figure 23:
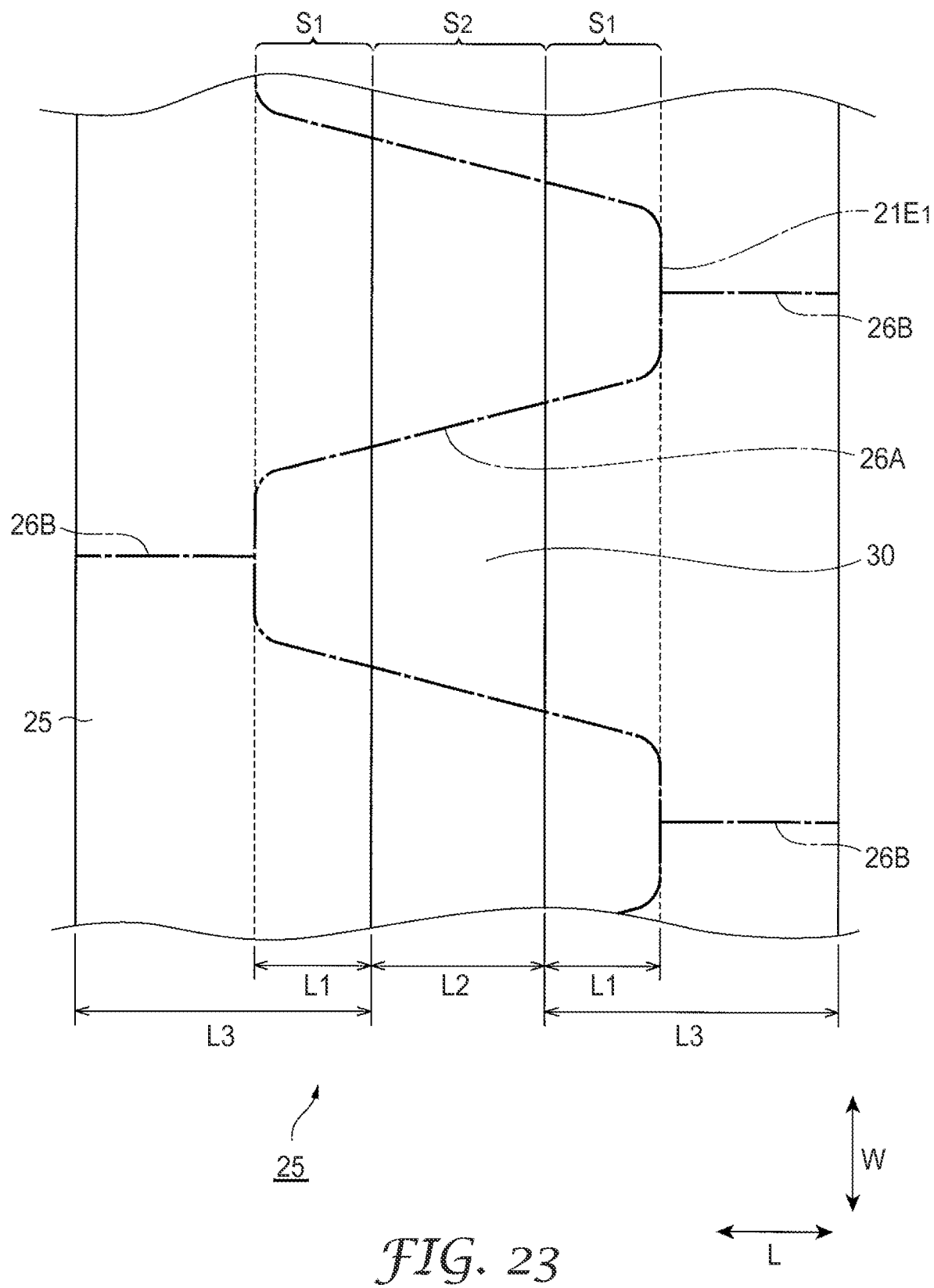
FIG. 23 shows an example of a method of manufacture of the fixing member.

FIGS. 22, 23, and 24 show an example of the method of manufacturing the fixing member, and the fixing member obtained by this method.

Figure 25:
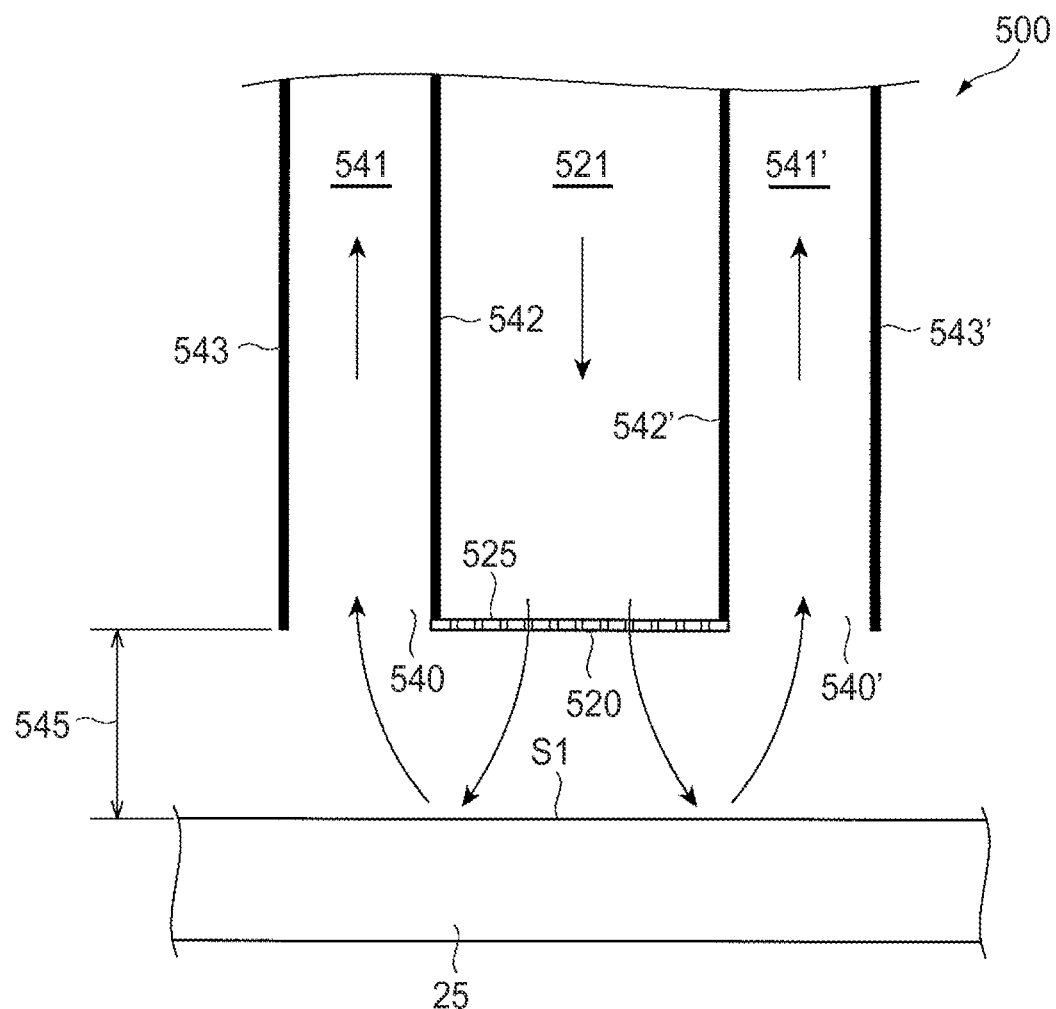
FIG. 25 shows an example of a method of heating the surface of the substrate.

Raw material base material 25 shown in FIG. 25 is a long sheet material that includes a plurality of portions corresponding to the base member of the manufactured fixing member.

As shown in FIG. 23, the long surface fastener 30 is continuously fitted along the longitudinal direction (width direction of the fixing member) W of the raw material base material 25, at a region $S_2$ in the center portion in the width direction (wrap-around direction of the fixing member) L of the raw material base material. In several aspects, the surface fastener 30 can be continuously fitted to the raw material base material 25 while the raw material base material 25 and the surface fastener 30, each in roll form, are fed out. By using long surface fastener 30, the process can be simplified. Alternatively, the surface fasteners can be fitted to the raw material base material corresponding to the surface fasteners 30 on the fixing members 20.

Fitting the surface fastener 30 to the raw material base material 25 can be carried out by a method selected from, for example, bonding, sewing, and fusion bonding. The method of fusion bonding that includes heating the surface of the raw material base material 25 and so on can be selected from the point of view of simplicity of the process, and so on.

In the present specification, the term 'fusion bonding' means joining two materials together by temporarily melting one or both of the materials to be joined. In several aspects of fusion bonding, the surface fastener 30 can be continuously fitted to the surface of the raw material base material 25 by a method that includes a step of heating the region $S_2$ of the surface of the raw material base material 25 and/or the rear surface of the surface fastener 30 (the surface on the side of the raw material base material 25) by impacting them with heating fluid; and a step of bringing the rear surface of the surface fastener 30 into contact with the region $S_2$ of the surface of the raw material base material 25, and fusion bonding the region $S_2$ of the surface of the raw material base material 25 to the rear surface of the surface fastener 30. The heating fluid can be selected from, for example, the surrounding air, dehumidified air, nitrogen, inert gas, or a combination thereof. In several aspects, the raw material base material 25 and the surface fastener 30 are each transported on a pair of opposing rolls rotating in the same direction, and the raw material base material 25 and the surface fastener 30 can be fusion bonded while held between the pair of rolls. In this method, by supplying the heating fluid from a curved nozzle along the outer circumference of the roll, provided near the position where the raw material base material 25 and the surface fastener 30 are held, the raw material base material 25 and the surface fastener 30 can be continuously heated until they contact. A fluid permeable sheet (perforated screen or the like) may be provided at the fluid outlet of the nozzle.

The linear velocity of the heating fluid may be, for example, less than Mach 0.5, or less than Mach 0.2. The linear velocity of the heating fluid may be in the order of several meters per second, for example, less than 50 meters per second, less than 25 meters per second, or less than 15 meters per second.

Heating for fusion bonding is not limited to a method using a heating fluid, for example, a method in which the raw material base material 25 is passed between a pair of heated rolls can be used.

Heating conditions such as the heating temperature and the heating time for the fusion bonding and so on can be set as appropriate so that the surface portion of the raw material base material 25 and/or the surface fastener 30 is at the temperature at which partial melting occurs to produce the fusion bonding. The heating temperature (for example the heating fluid temperature) may be not less than 120° C. or not less than 150° C., and not more than 600° C. or not more than 500° C. The heating time may be not less than one millisecond or two milliseconds, and not more than two seconds.

Before or after the step of fitting the surface fastener 30 to the raw material base material 25, or simultaneously with this step, the region $S_1$ which is adjacent to the region $S_2$ in the width direction L of the raw material base material 25 is heat treated. By heat treating the region $S_1$, the region $S_1$ can be made to have reduced engagement with the surface fastener as compared with before the heat treatment. If the raw material base material 25 is the fiber assembly, the fiber assembly on the surface portion is melted by the heating, so the fusion bonding occurs between fibers, and as a result, the density of fibers that can contribute to the engagement with the surface fastener (hooks, if the surface fastener is a hook member) is reduced.

In several aspects, the region $S_2$ can be continuously heat treated while moving the raw material base material 25 in the longitudinal direction. While moving the raw material base material 25 in the longitudinal direction, the region $S_2$ of the surface of the raw material base material 25 may be heat treated on the upstream side or the downstream side of the process of fitting the surface fasteners 30. Both steps may be carried out continuously, or after one step the other step may be carried out after temporarily rolling the raw material base material 25. While moving the raw material base material 25 in the longitudinal direction, the region $S_1$ can be continuously heat treated, but in this case, not only is the portion of the base member corresponding to the portion on the tip end $21E_1$ side of the surface fastener 30 heat treated, but also the surface on the opposite side (base end $21E_2$ side). As a result, in the fixing member 20 obtained, the engagement of the surface of the base member 21 on the tip end $21E_2$ side of the surface fastener 30 ($S_1'$ in FIG. 24) has reduced engagement with the surface fastener 30.

The method of heat treating the surface $S_1$ of the raw material base material 25 can be carried out by the same method as the fusion bonding for fitting the surface fasteners 30. In the case of the method using a heating fluid, for example, heating fluid may be supplied from a nozzle having a width corresponding to the region $S_1$, or heating fluid may be supplied from a nozzle having a width corresponding to the portion from the region $S_1$ to the region $S_2$, and the region $S_1$ may be heat treated at the same time as fusion bonding the surface fasteners 30.

FIG. 25 shows an example of a method of heat treating the surface $S_1$ of the raw material base material 25 by the method of impacting it with heating fluid. In the method shown in FIG. 25, a nozzle 500 includes a fluid outlet 520, and fluid auxiliary inlets 540, 540' provided on both sides thereof. A perforated screen 525 is provided in the fluid outlet 520, and heating fluid is supplied from here towards the surface $S_2$ of the raw material base material 25. The heating fluid is supplied through a fluid delivery channel 521 which is partitioned by partition walls 542, 542'. The heating fluid discharged from the fluid outlet 520 enters the fluid auxiliary inlets 540, 540', and flows in fluid removal channels 541, 541' partitioned by partition walls 542, 542'. The fluid delivery channel 521 and the fluid removal channels 541, 541' are separated by the partition walls 542, 542'. The distance 545 between the nozzle 500 and the raw material base material is, for example, 10 mm, 5 mm, or less than 2 mm. By adjusting the width of the nozzle 500, it is possible to heat only the region $S_1$, or to heat both the region $S_1$ and the region $S_2$ at the same time. In other words, by heating the surface of the raw material base material 25 from the region $S_2$ where the surface fastener is fitted to the region at the position corresponding to the tip end $21E_1$ of the base member (the portion from the region $S_2$ to the region $S_1$, in other words the portion of the region $S_2$ and $S_1$), it is possible to carry out the heating for fitting the surface fastener 30 and the heating for heat treating the surface of the raw material base material 25 to reduce the engagement with the surface fastener 30 at the same time. In this way, it is not necessary to increase the number of processes, and it is possible to easily manufacture the fixing member having a surface with reduced engagement with the surface fastener.

The heating conditions such as the heating temperature and the heating time and so on can be adjusted as appropriate to reduce the engagement with the surface fastener 30. For example, the lower limit of the heating temperature (for example the heating fluid temperature) may be 120° C. or 150° C., and the upper limit may be 500° C. or 400° C. The heating time may be not less than 0.5 milliseconds or not less than one millisecond, and not more than two seconds or not more than one second.

After fitting the surface fastener 30 to the region 52 and heat treating the region $S_1$, a laminate 26 of the raw material base material 25 and the surface fastener 30 is divided into a plurality of fixing members 20. Dividing the laminate 26 may be carried out by dividing the laminate in a periodic winding manner along the longitudinal direction (the width direction of the fixing member) W, then dividing the laminate 26 in the width direction (the wrap-around direction of the fixing member) L along the winding line 26A that includes ridge portions that include the portions that will become the tip end $21E_1$ of the base member, and dividing each divided part in the longitudinal direction (width direction of the fixing member) W along a cut line 26B that extends from a position corresponding to the valley portions of the winding line 26A to the edge of the raw material base material 25

The method of dividing the laminate 26 can be selected as appropriate from among methods normally used by persons skilled in the art. To enable the raw material base material 25 to be easily divided into the fixing members 20, the portions along the winding line 26A and/or the cut line 26B of the raw material base material 25 may be made fragile. For example, perforations or cuts to an intermediate depth may be formed in the surface of the raw material base material 25, or local thin portions may be formed in the base material. Alternatively, the raw material base material 25 may be completely cut at the winding line 26A and/or the cut line 26B to the extent that the shape of the raw material base material 25 is maintained in the processes necessary for fitting the surface fasteners and so on. In particular, completely cutting along the boundary 26B that extends in the width direction of the raw material base material 25 can be easily selected. The form of the lines dividing the laminate can be changed as appropriate in accordance with the shape of the fixing member 20 and so on.

EXAMPLES

In the following, further specific description of the present invention is provided through working examples. However, the present invention is not limited to the following working examples.

Example 1

A hook member 100 mm width and having diamond shaped openings was prepared (width 30 mm, 100 g/m$^2$, 1600 pins/inch$^2$, base thickness 80 μm, maximum width of umbrella portion 42 μm). The surface of polypropylene nonwoven fabric 50 g/m$^2$ was heated with 260° C. hot air over a width of 50 mm (hook member width+20 mm), and a hook member whose rear surface was heated to 210° C. was fitted thereto by fusion bonding. In this way, the hook member was fitted to the nonwoven fabic (base member), and a fixing member was obtained that was processed with heat on portions 10 mm wide on both sides of the hook member.

Example 2

A hook member 100 mm width and having diamond shaped openings was prepared (width 30 mm, 100 g/m², 1600 pins/inch², base thickness 80 μm, maximum width of umbrella portion 420 μm). The surface of polypropylene nonwoven fabric 60 g/m² was heated with 260° C. hot air over a width of 50 mm (hook member width+20 mm), and a hook member whose rear surface was heated to 210° C. was fitted thereto by fusion bonding. In this way, the hook member was fitted to the nonwoven fabric (base member), and a fixing member was obtained that was processed with heat on portions 10 mm wide on both sides of the hook member.

Example 3

A hook member 100 mm width without grooves or penetrations was prepared (width 30 mm, 65 g/m², 1600 pins/inch², base thickness 60 μm, maximum width of umbrella portion 350 μm). The surface of polypropylene nonwoven fabric 50 g/m² was heated with 190° C. hot air over a width of 50 mm (hook member width+20 mm), and a hook member whose rear surface was heated to 210° C. was fitted thereto by fusion bonding. In this way, the hook member was fitted to the nonwoven fabric (base member), and a fixing member was obtained that was processed with heat on portions 10 mm wide on both sides of the hook member.

Comparative Example 1

A hook member 100 mm width without grooves or penetrations was prepared (width 30 mm, 65 g/m², 1600 pins/inch², base thickness 60 μm, maximum width of umbrella portion 350 μm). The surface of polypropylene nonwoven fabric 60 g/m² was heated with 260° C. hot air over a width of 30 mm, and a hook member was fitted thereto by fusion bonding. In this way, the hook member was fitted to the nonwoven fabric (base member), and a fixing member was obtained.

Bending Stiffness

The bending stiffness of the fixing member was measured in bending tests using a Gurley testing machine, by the method shown in FIGS. 26 to 28, by fixing the hook member portion or the base member portion with the clamp. Test pieces having a length in the wrap-around direction of the fixing member of 25.4 mm (1 inch), and a length in the direction orthogonal to the wrap-around direction of 25.4 mm (1 inch) or 12.7 mm (0.5 inches) were used. The bending stiffness (bending stiffness A) of the fixing member was measured using test pieces cut from the portion where the hook member was provided, by fixing the test piece by sandwiching it in the clamp at the base member only as shown in FIG. 27, and the length L11 from the edge of the clamp (fixed end) 40E to the free end 40F of the test piece was set to 19.05 mm (0.75 inches). The bending stiffness (bending stiffness B) was measured using a strip-like test piece cut from a portion extending from the portion where the hook member was provided to the portion on the tip end side where the hook member was not provided, the test piece was fixed as shown in FIG. 28 by sandwiching the base member portion (portion where the hook member was not provided) in the clamp, the length L11 from the edge of the clamp (fixed end) 40E to the free end 40F of the test piece was set to 19.05 mm (0.75 inches), and the length L13 from the fixed end 40E to the portion of the test piece where the hook member was provided was set to a minimum value of 3.65 mm. The fixing member was tested forward and back in both the clockwise direction and the counterclockwise direction, and the average value of the bending stiffness was obtained. This measurement was repeated five times, and the average value was calculated as the bending stiffness of each test piece.

Peeling Test (1) Base Member-Side Test Piece

Double-sided adhesive tape (Sumitomo-3M industrial adhesive tape #465) was fixed to the rear surface of the portion of the base member from the grip portion to the surface fastener. Next, the grip portion was separated by cutting the base member along the edge of the surface fastener. The separated grip portion was applied to A4 side paper so that the edge of the paper and the edge on the surface fastener side of the grip portion were aligned. Next, the paper was cut along the wrap-around direction L, as shown in FIG. 29, to obtain the base member-side test piece having the width (W20) of 15 mm of the grip portion 21a attached to the edge of the strip of paper, and a length (L1) of 10 mm.

(2) Surface Fastener Side Test Piece

The remainder of the fixing member after separating the grip portion 21a was cut along the wrap-around direction, and a portion with width W22 of 25 mm including the portion where the surface fastener was provided was obtained as the test piece. The obtained surface fastener side test piece was fixed to the stainless steel panel 62 as shown in FIG. 30, using adhesive tape.

(3) 90 Degree Peeling Test

As shown in FIG. 31, the stainless steel panel 62 was placed on the platform 64, and the base member-side test piece (grip portion 21a) was placed on the surface fastener 30. The position of the base member-side test piece was a distance 5 mm from the edge of the grip portion 21a side of the surface fastener 30 in the wrap-around direction L, and positioned in the center in the width direction W of the surface fastener. In this state, a 500 g weight 68 was placed on the base member-side test piece. Next, a 500 g weight 66 was suspended from the end of the strip of paper 60. Three seconds after starting to suspend the weight 66, the weights 66, 68 were removed.

Then, as shown in FIG. 32, the peeling strength was measured while pulling and peeling the base member test piece at the speed 300 mm/minute at 90 degrees with respect to the surface of the surface fastener 30 and the wrap-around direction L, from the tip end 21E$_1$ side. The maximum value of the peeling strength in the process of peeling off the whole base member test piece was recorded.

TABLE 1

| | | Example 1 | Example 2 | Example 3 | Comparative Example 1 | Commercial product 1 | Commercial product 2 |
|---|---|---|---|---|---|---|---|
| Hoop member | Opening | Diamond-shaped | Diamond-shaped | None | None | None | None |
| | Areal mass g/m² | 100 | 100 | 65 | 65 | 100 | 100 |

TABLE 1-continued

|  |  | Example 1 | Example 2 | Example 3 | Comparative Example 1 | Commercial product 1 | Commercial product 2 |
|---|---|---|---|---|---|---|---|
| Nonwoven material | Areal mass g/m² | 50 | 60 | 50 | 60 |  |  |
| Bending Stiffness mgf | A | 17.0 | 21.8 | 77.6 | 191.3 | 210.2 | 228.0 |
|  | B | 11.6 | 24.7 | 15.1 | 38.5 | 45.8 | 38.1 |
| Maximum value of 90-degree peeling strength N/15 mm |  | 0.02 | 0.04 | 0.02 | 0.15 | 0.2 | 0.18 |

The maximum values of the bending stiffness and the peeling strength of the Working Examples and Comparative Examples of fixing member are shown in Table 1. Likewise the fixing members taken from commercial diapers (commercial product 1, commercial product 2) are shown in Table 1. The fixing members according to the working examples using hook members having grooves, penetrations, or openings, or with small aereal weight, and nonwoven fabric had bending stiffness of the hook member portion of not more than 150 mg. Furthermore, the maximum value of the 90-degree peeling strength between the portion equivalent to the grip portion of the fixing members according to the working examples was not more than 0.10N/15 mm. Using the fixing members according to the working examples, the stability for preventing displacement and the ability to follow movements at the locations fixed at the front waist portion and the rear waist portion of a diaper is excellent, and during use it is possible to prevent the grip portion that becomes unintentionally folded back from staying in that state. On the other hand, the fixing member according to Comparative Example 1 was stiff, and the ability to follow movements was not sufficient. Note that because the fixing member itself was stiff, the problem of the grip portion of the fixing member folding back is more difficult to occur compared with the working examples, but if the grip portion was folded back, it easily adhered to the hook member. The fixing members of the commercial products were stiff, and although the area over which the hook member was placed on the fixing member of the commercial product was small, the portion corresponding to the grip portion easily adhered to the hook member.

REFERENCE NUMERALS 1 absorbent article (diaper),
10 main body portion,
14 loop member,
20 fixing member,
21 base member,
21a portion (grip portion) of the base member on the tip end side of the surface fastener
21c folded portion of the base member
21$E_1$ tip end of the base member
21$E_2$ base end of base member
25 raw material base material
26 laminate
30 surface fastener (hook member)
31 base
32 hook
33 groove or penetration
33a slit-like penetration
33b slit-like groove 34 opening
35 strand
36 linking portion
40 clamp
40E fixed end
40F free end
L11 length of test piece from fixed end to free end
L13 length of the test piece from the fixed end to the portion where the surface fastener 30 is provided
L wrap-around direction of the fixing member W width direction of the fixing member
$S_1$ surface on the grip portion side of the surface fastener
$S_2$ region of the surface of the base member or the raw material base material where the surface fastener is provided.

What is claimed is:

1. A fixing member comprising: a sheet-like base member; and
a surface fastener provided on top of the base member, wherein
the surface fastener covers a surface of the base member at a position separated from a tip end of the base member, a minimum value of bending stiffness of the fixing member, as determined via a bending test using a Gurley tester, being 150 mgf or less, the bending test being performed using a strip-shaped test piece cut from a portion where the surface fastener is provided by anchoring an end of the test piece using a clamp so that a length from the anchored end of the test piece to the free end thereof is 19.05 mm; and
engagement with the surface fastener is minimized on the surface of the base member on a side on which the surface fastener is provided in a part closer to the tip end than the surface fastener, wherein
an opening is provided in the base member, a penetration is provided in the surface fastener, and the opening of the base member and the penetration of the surface fastener are overlapped on the fixing member and set such that the base member and the surface fastener of the fixing member can flexibly change shapes.

2. The fixing member according to claim 1, wherein the surface of the base member in which the engagement with the surface fastener is minimized has a maximum 90-degree peel strength with respect to the surface fastener of 0.10 N/15 mm or less.

3. The fixing member according to claim 1, wherein the surface of the base member wherein engagement with the surface fastener is minimized is constituted by a heat-treated fiber assembly.

4. The fixing member according to claim 1, wherein the bending stiffness of the fixing member as determined via the bending test using the Gurley tester is 30 mgf or less, the bending test being performed using a strip-shaped test piece cut from a part extending from the part where the surface fastener is provided to a part at the tip end where the surface fastener is not provided by anchoring the end where the surface fastener is not provided of the test piece using a clamp so that the length from the anchored end of the test piece to the free end thereof is 19.05 mm and the minimum length from the anchored end to the part of the test piece where the surface fastener is provided is 3.65 mm.

5. The fixing member according to claim 1, wherein the part closer to the tip end than the surface fastener of the base member is folded back.

6. An absorbent article comprising the fixing member according to claim 1.

7. A method of manufacturing the fixing member according to claim 1,
comprising a step of heat-treating a part of a surface of a side of a base member on which a surface fastener is present so as to minimize engagement with the surface fastener;
the heat-treated surface being a fiber assembly.

8. The method according to claim 7, further comprising the steps of:
preparing an elongated raw material base material constituting a plurality of the base members;
attaching the surface fastener to a surface of the raw material base material;
dividing a laminate comprising the raw material base material and the surface fastener attached to the raw material base material into a plurality of the fixing members;
wherein
the step of heat-treating the part of the surface of the side of the base member on which the surface fastener is present so as to minimize the engagement with the surface fastener being a step of heat-treating an area of the surface of the raw material base material between the area where the surface fastener is attached and a position corresponding to the tip ends of the base members so as to minimize the engagement with the surface fastener.

9. The method according to claim 8, wherein the step of attaching the surface fastener to the surface of the raw material base material is performed by heating the area of the surface of the raw material base material to which the surface fastener is attached, and
the step of attaching the surface fastener and the step of heat-treating the part of the surface of the side of the base member on which the surface fastener is present so as to minimize the engagement with the surface fastener are simultaneously performed by continuously heating the area on the surface of the raw material base material where the surface fastener is attached and the area between the area where the surface fastener is attached and the position corresponding to the tip ends of the base members while moving the raw material base material in a lengthwise direction thereof.

10. The method according to claim 8, wherein: the step of dividing the laminate into the plurality of the fixing members includes:
dividing the laminate in a widthwise direction along an undulating line that periodically undulates in a lengthwise direction of the laminate and comprises peaks including a part forming the tip end, and
dividing the divided pieces in the lengthwise direction at positions corresponding to dips in the undulating line.

* * * * *